United States Patent [19]

Goetz

[11] Patent Number: 5,334,333
[45] Date of Patent: Aug. 2, 1994

[54] ELECTROACTIVE COMPOUNDS, COMPOSITIONS AND DEVICES AND METHODS OF MAKING THE SAME

[75] Inventor: Frederick J. Goetz, Wilmington, Del.

[73] Assignee: Elf Atochem North America, Inc., Philadelphia, Pa.

[21] Appl. No.: 629,781

[22] Filed: Dec. 17, 1990

[51] Int. Cl.[5] .............. F21V 9/00; C07C 45/00; C07C 49/115
[52] U.S. Cl. .................. 252/582; 359/328; 359/329; 568/321; 568/327; 544/241; 544/224; 544/242; 544/335; 544/334; 544/298; 544/319; 546/79; 546/152; 546/153; 546/339; 549/29; 549/43; 549/44; 549/51; 549/460; 549/429; 548/100; 548/120; 548/121; 548/146; 548/181; 548/182; 548/215; 548/217; 548/225; 548/226; 548/300.1; 548/302.7; 548/452; 548/400
[58] Field of Search .............. 568/321, 327; 252/582; 359/328, 329; 544/241, 224, 242, 335, 334, 298, 319; 546/79, 152, 153, 339; 548/100, 120, 121, 146, 181, 182, 215, 217, 225, 226, 300.1, 302.7, 452, 400; 549/29, 43, 44, 51, 460, 429

[56] References Cited

U.S. PATENT DOCUMENTS

| | | | |
|---|---|---|---|
| 3,413,353 | 11/1968 | Nauta | 568/327 |
| 3,879,468 | 4/1975 | Durden et al. | 568/327 |
| 4,767,169 | 8/1988 | Teng et al. | 350/96.14 |

FOREIGN PATENT DOCUMENTS

| | | |
|---|---|---|
| 245710 | 9/1962 | Australia . |
| 617120 | 3/1961 | Canada . |
| 0364313 | 4/1990 | European Pat. Off. . |
| 867138 | 7/1962 | France . |
| 56-6652 | 2/1981 | Japan . |
| 251564 | 2/1990 | Japan . |
| 2135264 | 5/1990 | Japan . |

OTHER PUBLICATIONS

"Nonlinear Optical Properties of Organic and Polymeric Materials," edited by David J. Williams, American Chemical Society, Washington, DC (1985).

David J. Williams, "Organic Polymeric and Non-Polymeric Materials with Large Optical Nonlinearities," Angew. Chem Int. Ed. Engle 23, pp. 690-703 (1984).

Primary Examiner—Philip Tucker
Attorney, Agent, or Firm—Panitch Schwarze Jacobs & Nadel

[57] ABSTRACT

The present invention relates to electroactive compounds capable of undergoing a change in light absorption and refraction due to an applied electric field and a permanent change in refraction due to exposure to predetermined bands of optical radiation. The present invention also relates to electroactive compositions containing such electroactive compounds, electrooptical components comprised of such electroactive compositions and electrooptical devices comprised of such electrooptical components, as well as novel processes of making the same.

6 Claims, 8 Drawing Sheets

ELECTROACTIVE COMPOUNDS, COMPOSITIONS AND DEVICES AND METHODS OF MAKING THE SAME

BACKGROUND OF THE INVENTION

The present invention relates to electroactive compounds, namely, compounds capable of undergoing a change in light absorption and refraction when subjected to an outside influence, the use of such electroactive compounds in compositions to make electroactive compositions, the use of such electroactive compositions to make electrooptical devices, such as modulators of light in integrated optic or fiber optic systems, as well as methods of making the foregoing compounds, compositions and devices.

The basis of the many aspects of the various embodiments of the present invention is the novel electroactive compound within the novel classes of electroactive compounds of the present invention. The electroactivity of the compounds, and therefore, the compositions and devices incorporating them, is based upon the delocalized pi-electron system which exhibit nonlinear optical response. In addition, the electroactive compounds of the present invention have an unusual ability to undergo a permanent change in refraction upon exposure to certain predetermined wavelengths of optical radiation which permits a type of photolithographic process to create optical waveguides in compositions containing the electroactive compounds of the present invention.

Electrooptical modulators, switches and optical parametric devices based upon the nonlinear optical properties of materials are known in the art. Generally, these devices have utilized inorganic crystals, e.g., $LiNbO_3$. In addition, due to the electronic states associated with the effect, the organic crystalline materials not only have large intrinsic second order nonlinear optical susceptibilities, but potentially possess very fast switching time.

It is known that organic and polymeric materials with large delocalized pi-electron systems can exhibit nonlinear optical response, which in many cases is a much larger response than by inorganic substrates.

In addition, the properties of organic and polymeric materials can be varied to optimize other desirable properties, such as mechanical and thermooxidative stability and high laser damage threshold, with preservation of the electronic interactions responsible for nonlinear optical effects.

Thin films of organic or polymeric materials with large second order nonlinearities in combination with silicon-based electronic circuitry have potential as systems for laser modulation and deflection, information control in optical circuitry, and the like.

Other novel processes occurring through third order nonlinearity such as degenerate four-wave mixing, whereby real-time processing of optical fields occurs, have potential utility in such diverse fields as optical communications and integrated optical circuit fabrication.

Of particular importance for conjugated organic systems is the fact that the origin of the nonlinear effects is the polarization of the pi-electron cloud as opposed to displacement or rearrangement of nuclear coordinates found in inorganic materials.

Nonlinear optical properties of organic and polymeric materials was the subject of a symposium sponsored by the ACS division of Polymer Chemistry at the 184th meeting of the American Chemical Society, September 1982. Papers presented at the meeting are published in D. C. Williams, Ed., ACS Symposium Series 233, American Chemical Society, D. C. (1983). The above recited publications are incorporated herein by reference.

The fundamental concepts of nonlinear optics and their relationship to chemical structures can be expressed in terms of dipolar proximation with respect to the polarization induced in an atom or molecule by an external field. The concepts and theory are now well known to those skilled in the art as represented by the papers published in the ACS Symposium Series 233 cited and incorporated herein by reference above.

SUMMARY OF THE INVENTION

One aspect of the present invention relates to an electroactive compound capable of undergoing a reversible change in light absorption and refraction due to an applied electric field and a permanent change in refraction due to exposure to predetermined bands of optical radiation, the compound having structure 1:

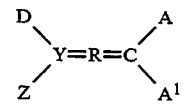

and a resonance canonical structure 1A:

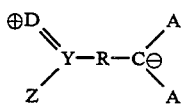

wherein

D comprises $D^1$=X— in structure 1, corresponding to $\oplus D^1$—X= in resonance canonical structure 1A, or $D^2$=C— in structure 1, corresponding to $\oplus D^2$—C= in resonance canonical structure 1A, where $D^1$ is an electron donating, substituted or unsubstituted unsaturated heterocyclic organic ring system having a members in the ring system, one to (a−1) members being at least one electron donating heteroatom having one or two lone electron pairs, the $D^1$ substitutents being bonded to a carbon or to a heteroatom of the ring system and being J or L;

X is a trivalent atom having one lone electron pair orbital or a substituted or unsubstituted tetravalent atom, the substituents for the tetravalent atom of X being J, L, $R^1$, $R^2$, G—$R^3$ or Q;

where D is $D^1$=X— or $\oplus D^1$—X=,

Y is C, or a trivalent atom having one lone electron pair orbital;

where Y is a trivalent atom having one lone electron pair orbital, Z is a lone electron pair; and where Y is C, Z is independently $D^1$=X— in structure 1 corresponding to $\oplus D^1$—X= in resonance canonical structure 1A, or J, L, $R^1$, $R^2$, G-$R^3$ or Q;

$D^2$=C— in structure 1 corresponding to $\oplus D^2$—C= in resonance canonical structure 1 is a substituted or unsubstituted aromatic carbocyclic or substituted or unsubstituted aromatic heterocyclic ring system, where the C of $D^2$=C— or $\oplus D^2$—C= is a member of the ring system having b members and $J_c$ substituents, where c is zero to (b−1) and each J substituent is the same or different, $D^2=C-$ or $\oplus D^2-C=$ further having from zero to (b−c) additional substituents, the additional substituents being $R^1$, $R^2$, $G-R^3$ or Q;

where D is $D^2=C-$ or $\oplus D^2-C=$,

Y is C; and

Z is a substituted or unsubstituted aromatic carbocyclic or a substituted or unsubstituted aromatic heterocyclic ring system having d members, wherein the substituents are zero to (d−1) same or different J, L, $R^1$, $R^2$, $G-R^3$ or Q substituents;

R is a diradical comprising a substituted or unsubstituted aromatic carbocyclic ring system of e members or substituted or unsubstituted aromatic heterocyclic ring system of f members, wherein the substituents are zero to (e−2) or (f−2) same or different J, L, $R^1$, $R^2$, $G-R^3$ or Q substituents for the carbocyclic and heterocyclic ring systems, respectively;

A and $A^1$ are independently each an electron-withdrawing L group or A and $A^1$ together may form a substituted or unsubstituted ring system when the L group contains a J substituent, where the substituents for the A—$A^1$ ring system are J, L, $R^1$, $R^2$, $G-R^3$ or Q;

G is a diradical comprising substituted or unsubstituted —(—HC=CH—)$_m$13 , where m is an integer from 1 to 10, substituted or unsubstituted —(CH$_2$)$_n$—, where n is an integer from 1 to 22, a substituted or unsubstituted aromatic ring system of 6 to 16 carbons or a substituted or unsubstituted aromatic heterocyclic ring system of 5 to 14 members in the ring system, the members being carbon atoms and 1 to (g−1) heteroatoms, where g is the number of members in the heterocyclic ring system, the heteroatom being one or more of N, P, As, Sb, 0, S, Se or Te, the G substituents being j$^1$ or L$^1$ with the proviso that the maximum number of G substituents is 6;

$G^1$ and $G^2$ each independently have the same definition as G;

J is an electron donating group —(CH$_2$)$_n$—$R^1$, —S—$R^1$, —O—$R^1$, —N($R^1$)($R^2$), —G—$R^1$, —(CH$_2$)$_n$—G—$R^1$, —S—G—$R^1$, —O—G—$R^1$, —N(-$G^1$—$R^1$)($G^2$—$R^2$); j$^1$ is —(CH$_2$)$_n$—$R^1$, —S—$R^1$, —O—$R^1$ or —N($R^1$)($R^2$);

j$^2$, j$^3$ and j$^4$ each independently have the same definition as J;

L is —C≡N, —N=O, —NO$_2$, —C(=O)—j$^2$,

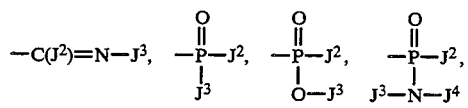

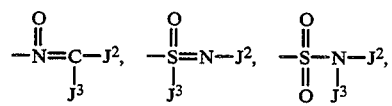

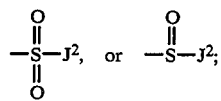

$L^1$ independently has the same definition as L;

$R^1$ and $R^2$ are independently H, F, Cl, Br, I, Q, alkyl of 1 to 22 carbons, cycloalkyl of 3 to 22 carbons, a substituted or unsubstituted aromatic ring system of 6 to 16 carbons or a substituted or unsubstituted aromatic heterocyclic ring system of 5 to 14 members in the ring system, the members being carbon atoms and 1 to (h−1) heteroatoms, where h is the number of members in the heterocyclic ring system, the heteroatom being one or more of N, P, As, Sb, O, S, Se or Te, the $R^1$ or $R^2$ substituents being $J^1$ or $L^1$ with the proviso that the maximum number of $R^1$ or $R^2$ substituents is 6;

$R^3$ is H, F, Cl, Br, I, Q, alkyl of 1 to 22 carbons or cycloalkyl of 3 to 22 carbons; and Q is a polymerizable group, the polymerizable group being alpha,beta-unsaturated carbonyl of 4 to 26 carbons, vinyl ether of 3 to 25 carbons, carboxylic acid of 2 to 23 carbons, ester of 3 to 45 carbons, alcohol of 1 to 22 carbons, alkyl amine of 1 to 44 carbons, 1-substituted or 1,1-substituted alkylene of 2 to 44 carbons, or a polymerizable group of 1 to 44 carbons containing a nucleophilically replaceable group of zero to 22 carbons, the Q substituents being J, L, $R^1$, $R^2$, $G-R^3$.

Another aspect of the present invention relates to novel chemical compounds used as intermediates to make certain of the novel electroactive compounds of the present invention. The intermediate compounds have the following respective structures:

Aldehyde compounds

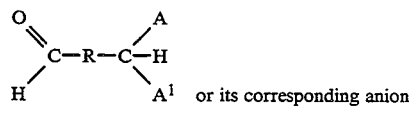

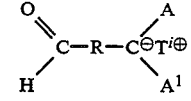

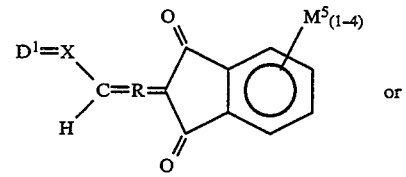

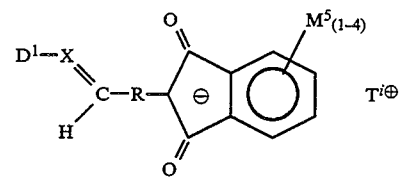

wherein $D^1$, X, R, A and $A^1$ are as previously or subsequently defined herein, $T^i\oplus$ is a stable metallic or nonmetallic cation, and i is an integer of 1 to 4; and

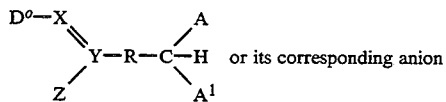

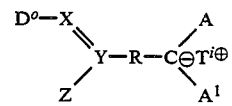

wherein $D^o$ is an electron donating substituted or unsubstituted unsaturated heterocyclic ring system of 4 to 20 members in the ring system, the members being carbon and 1 to (j−1) heteroatoms, wherein j is the number of atoms in the ring system, at least one carbon atom of the ring system being bonded to a heteroatom of the ring system by a double bond, the heteroatom being any of N, P or As;

Y is C, or a trivalent atom having one lone electron pair orbital;

where Y is a trivalent atom having one lone electron pair orbital, Z is a lone electron pair; and where Y is C, Z is independently $D^o\!=\!\!X\!-\!$, J, L, $R^1$, $R^2$, G—$R^3$ or Q; and X, R, A and $A^1$ are as previously or subsequently defined herein.

Another aspect of the present invention relates to a novel process of making the novel compounds where D is $D^1\!=\!\!X\!-\!$ or $\oplus D^1\!-\!\!X\!=\!$ where $D^1$ is substituted with a J or L group. This process is based upon the reaction of a substituted heterostilbene by transition metal catalyzed replacement of the substituent by a carbanion with at least one alpha-hydrogen atom.

Another novel process based on the present invention for preparing the novel compounds where D is $D^1\!=\!\!X\!-\!$ or $+ D^1\!-\!\!X\!=\!$ is based on the reaction with an appropriately substituted heterocyclic cation with a novel aldehyde intermediate substituted with an acidic carbon atom. The novel aldehyde is produced by reacting an aldehyde containing a leaving group with a carbanion containing an alpha-hydrogen atom and containing two electronic accepting groups.

A still further novel process according to the present invention of making an inventive electroactive compound where D is $D^2\!=\!\!C$ or $\oplus D^2\!-\!\!C\!=\!$ and Y is C, comprises reacting a starting compound having a structure

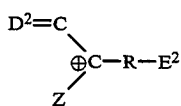

and a resonance canonical structure

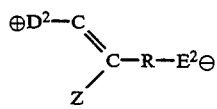

where $E^2$ is a group which can exist as a stable anion $E^2 \ominus$ or, when present as H—$E^2$, H—$E^2$ is acidic relative to organic polar aprotic solvents, with a carbanion containing an alpha-H atom having a structure

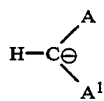

under conditions sufficient to form the compound of claim 1 having a structure

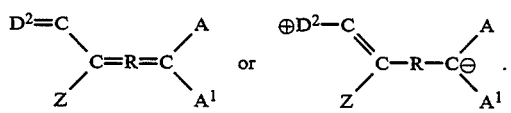

Further, another aspect of the present invention relates to a composition capable of undergoing a reversible change in light absorption and refraction due to an applied electric field and a permanent change in refraction due to exposure to predetermined bands of optical radiation comprising a matrix in which molecules of the electroactive compound of the present invention, each of which has a major axis, are oriented by application of an applied electric field in a matrix material comprising a liquid, a liquid crystal, a polymeric material or a crystal, such that the major axes of the molecules of the electroactive compound are aligned in the same direction and their electric moments are oriented in the same direction so as to be polarized.

Still another aspect of the invention relates to an electrooptical component comprising a body made of a composition containing an electroactive compound according to the present invention oriented within the composition to be capable of undergoing a reversible change in absorption and refraction due to an applied electric field and a permanent change in refraction due to exposure to predetermined bands of optical radiation, and a waveguide for transmitting light, the waveguide following polling being formed within the body between body portions adjacent opposite sides of the waveguide, the body portions having a first index of refraction, the waveguide having a second index of refraction higher than the first index of refraction of the body portions. Additional waveguides could be formed in the body.

Another aspect of the present invention relates to an electrooptical component capable of modulating light through an optical fiber when the component is optically connected to the optical fiber, the component comprising a core including an optical waveguide, the waveguide having two end faces, the core and waveguide comprising a composition containing an electroactive compound according to the present invention oriented within the composition to be capable of undergoing a reversible change in absorption and refraction due to an applied electric field, and core portions adjacent to the waveguide, the core portions having a first index of refraction, the waveguide having a second index of refraction higher than the first index of refraction of the adjacent core portions, opposed cladding layers overlying portions of the waveguide which are adjacent to the core portion but not the end faces of the waveguide, and one of each of a pair of electrodes overlying the opposed cladding layers.

Multiple waveguides can be formed in the same core or other layers forming additional cores. Likewise, the placement of the electrodes in such components can be varied to other suitable locations relative to the waveguide(s) to obtain other similar electrooptical effects.

Electrooptical devices formed from the electrooptical components of the present invention are other aspects of this invention.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE PREFERRED EMBODIMENTS

Electroactive Compounds

Figure 1:
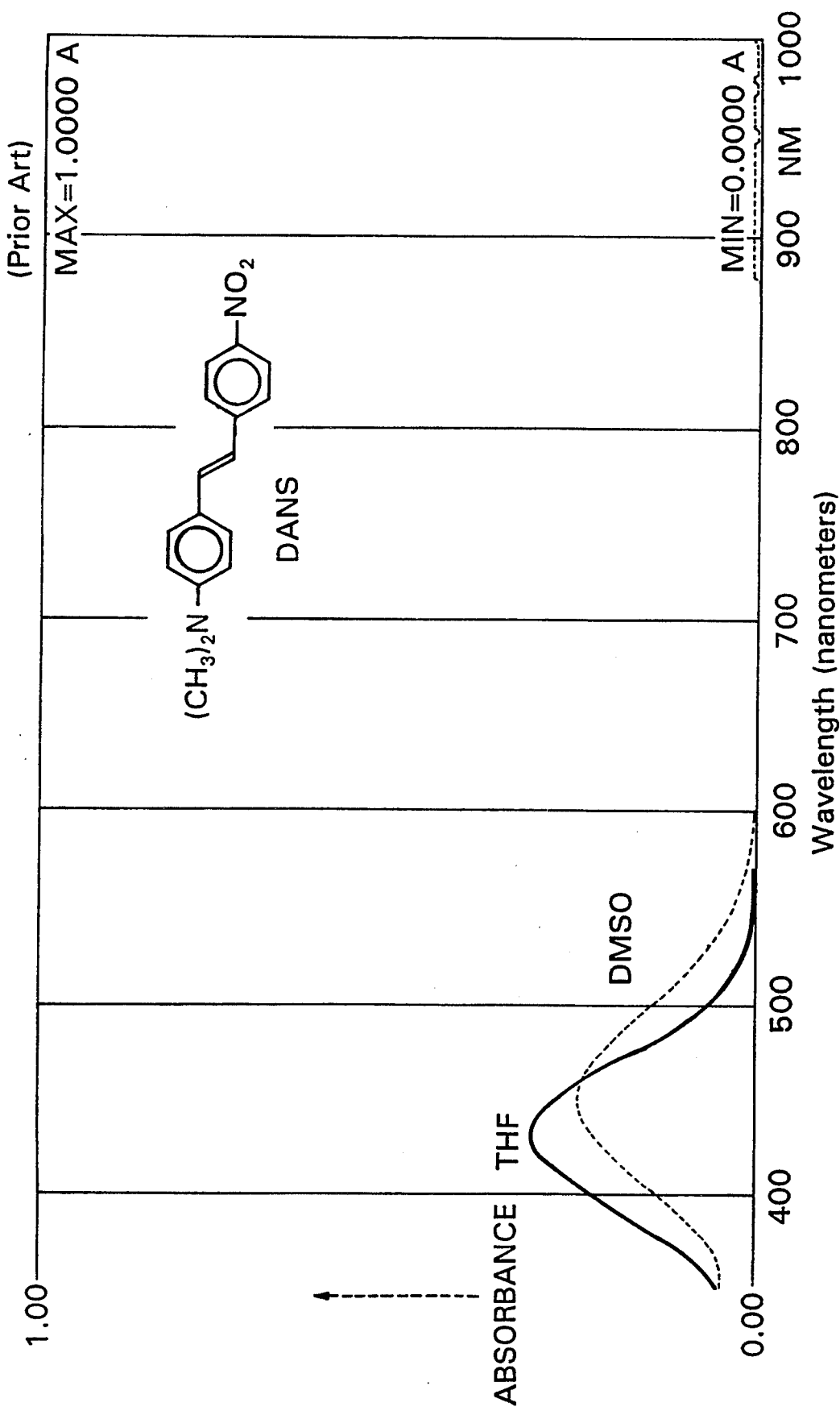
FIG. 1 is an absorption spectrogram indicating the solvatochromism exhibited by a first prior art electroactive compound, 4-(N,N-dimethylamino)-4'-nitrostilbene (DANS).

As indicated above, the various aspects of the present invention are based upon the discovery of novel electroactive compounds having nonlinear optical properties which are capable of undergoing a reversible change in light absorption and refraction due to an applied electric field and a permanent change in refraction due to exposure to predetermined bands of optical radiation. The compounds have the general structure 1:

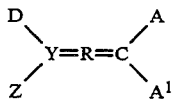

and an equivalent or corresponding resonance canonical structure 1A:

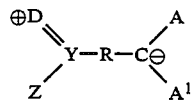

The definition of each component of the compounds of the present invention, and various substituent groups are set forth above under the Summary of the Invention.

As indicated in structure 1A, the molecules of the novel compounds have a large dipole moment along a long axis of the molecule. One end of the molecule is deemed to be electropositive by virtue of the presence of electron donating groups, namely, the $\oplus D$ group, whereas the opposite end is deemed to be electronegative by virtue of the presence of electron-accepting or withdrawing groups A and $A^1$. Because of their high level of electric polarization (large dipole moment), the molecules of the novel compounds will become highly oriented in various matrices when subjected to an orientation force, such as an applied electric field, stretching, compressing or con%bination of stretching or compression in the presence of a static electric field. The orientation of the molecules in the selected matrix will be such that the poles of the molecule are contrapolar to the polarization of the electrodes in the typical case of orientation in a static electric field when the compound is placed in a matrix between a positive electrode and a negative electrode. In the case of orientation by stretching or compression, in the presence of a static electric field the polarized molecules tend to become aligned with respect to each other anisotropically with the electropositive ends of the molecules being in the same general direction (say, in concept, the "left" end as structure 1A is written), opposite to the electronegative end (say, in concept, the "right" end as structure 1A is written) of the same molecule. The present molecules are characterized by their ability to maintain this anisotropic alignment in a matrix to form an electroactive composition.

The novel electroactive compounds of the present invention have the broad general structure described above in the summary of the invention. Preferred compounds are those having structure 1 or 1A wherein there are 4 to 20 a members of the ring system of $D^1$;

there are 4 to 20 b members of the ring system of $D^2=C-$ or $\oplus D^2-C=$;

there are 4 to 20 d members of the ring system of Z;

there are 6 to 20 e members of the aromatic carbocyclic ring system of R and there are 4 to 20 f members of the aromatic heterocyclic ring system of R;

any of the heteroatoms of any of the heterocyclic ring systems of $D^1$, $D^2=C-$ or $\oplus D^2-C=$, Z, R or G are independently N, P, As, Sb, O, S, Se or Te;

the trivalent atom of X is N, P, As or Sb and the tetravalent atom of X is C, Si or Ge; and the trivalent atom of Y is N, P, As or Sb.

At present, more preferred compounds are those in which the components and the substituents are defined as follows, with reference to Tables 1 through 9 forming the last portion of this specification immediately prior to the claims. In the Tables, the symbols $E^1$ and E independently represent the indicated elements of Group VA and Group VIA of the Periodic Table, respectively. Thus, for example, if E appears more than once in the same radical or diradical contained in the Tables, each E may be the same or different, even in the same radical, except as specified hereinafter. Also in the Tables, the various substituents that may be substituted on the ring systems have been referred to generically as M, $M^1$, $M^2$, $M^3$ and $M^4$, where the subscript "*" signifies the number of available valences for the substituents which were varied in any given ring system or portion thereof. Thus, reference should be made to the claims or this written description to determine the permissible substituents for the ring systems, since the substituents are depicted generically in the Tables.

The compounds of the present invention in a presently more preferred form are those in which the components of Structure 1or 1A are defined as follows:

$D^1$ is any radical set forth in

Table 2, where any $E^1$ is N, P or As,

Table 3, where any $E^1$ is N, P or As and any E is O, S, Se or Te,

Table 4, where any $E^1$ is N, P or As and any E is O, S, Se or Te,

Table 5, where any E is O, S, Se or Te;

$D^2$=C— is any radical set forth in Table 6 or Table 7, where any $E^1$ is N, P or As and any E is O, S, Se or Te;

the trivalent atom of X is N or P and the tetravalent atom of X is C, and where X is C, any substituted or unsubstituted aromatic carbocyclic ring system which is a substitutent of X is any radical set forth in Table 6, and where X is C and substituted with a substituted or unsubstituted aromatic heterocyclic ring system, the heterocyclic ring system is any radical set forth in Table 7, where any $E^1$ is N, P or As and E is O, S, Se or Te;

where D is $D^1$=X— or $\oplus D^1$—X=, the trivalent atom of Y is N or P and the tetravalent atom of Y is C, and where Y is C, any substituted or unsubstituted aromatic carbocyclic ring system which is a substituent of Y is any radical set forth in Table 6, and where Y is C and substituted with a substituted or unsubstituted aromatic heterocyclic ring system, the heterocyclic ring system is any radical set forth in Table 7, where any $E^1$ is N, P or As and any E is O, S, Se or Te;

further where D is $D^1$=X— or $\oplus D^1$—X= and Y is C, Z is any radical set forth in Table 2, where any $E^1$ is N, P or As, Table 3, where any $E^1$ is N, P or As and any E is O, S, Se or Te, Table 4, where any $E^1$ is N, P or As and any E is O, S, Se or Te, Table 5, where any E is O, S, Se or Te;

where D is $D^2$=C— or $\oplus D^2$—C=, Z is any radical set forth in Table 6 or Table 7, where any $E^1$ is N, P or As and any E is O, S, Se or Te;

where G, $G^1$ or $G^2$ are independently a substituted or unsubstituted aromatic ring system, the ring system is any diradical R8 set forth in Table 8, and where G, $G^1$ or $G^2$ is a substituted or unsubstituted aromatic heterocyclic ring system, the heterocyclic ring system is any diradical R9 set forth in Table 9, where any $E^1$ is N, P or As and any E is O, S, Se or Te;

where R is a substituted or unsubstituted diradical comprising an aromatic carbocyclic ring system, the ring system is any diradical R8 set forth in Table 8, and when R is a substituted or unsubstituted aromatic heterocyclic ring system, the heterocyclic ring system is any diradical R9 set forth in Table 9, where any $E^1$ is N, P or As and any E is O, S, Se or Te; and if $R^1$ or $R^2$ is attached to O or N, $R^1$ and $R^2$ are independently H, Q, alkyl of 1 to 22 carbons, cycloalkyl of 3 to 22 carbons, or a substituted or unsubstituted aromatic ring system of 6 to 16 carbons or a substituted or unsubstituted aromatic heterocyclic ring system of 5 to 14 members in the ring system, the members being carbon atoms and 1 to (h—1) heteroatoms, where h is the number of members in the heterocyclic ring system, the heteroatom being one or more of N, P, As, Sb, O, S, Se or Te, the $R^1$ or $R^2$ substituents being J1 or $L^1$ with the proviso that the maximum number of $R^1$ or $R^2$ substituents is 6.

The presently most preferred form of the electroactive compounds of the present invention having formulas 1 or 1A are those in which the components are defined as follows:

$D^1$ is any radical set forth in

Table 2, where any $E^1$ is N or P,

Table 3, where any $E^1$ is N or P and any E is O, S or Se,

Table 4, where any $E^1$ is N or P, and any E is O, S or Se,

Table 5, where E is O, S or Se;

$D^2$=C— is any radical set forth in Table 6 or Table 7, where any $E^1$ is N and any E is O, S or Se;

the trivalent atom of X is N and the tetravalent atom of X is C, and where X is C, any substituted or unsubstituted aromatic carbocyclic ring system which is a substitutent of X is any radical set forth in Table 6, and where X is C and substituted with a substituted or unsubstituted aromatic heterocyclic ring system, the heterocyclic ring system is any radical set forth in Table 7, where any $E^1$ is N and any E is O or S;

where D is $D^1$=X— or $\oplus D^1$—X=, the trivalent atom of Y is N and the tetravalent atom of Y is C, and where Y is C, any substituted or unsubstituted aromatic carbocyclic ring system which is a substituent of Y is any radical set forth in Table 6, and where Y is C and substituted with a substituted or unsubstituted aromatic heterocyclic ring system, the heterocyclic ring system is any radical set forth in Table 7, where any $E^1$ is N and any E is O or S;

further where D is $D^1$=X— or $\oplus D^1$-X= and Y is C, Z is any radical set forth in Table 2, where any $E^1$ is N or P, Table 3, where any $E^1$ is N or P and any E is O, S or Se, Table 4, where any $E^1$ is N or P and any E is O, S or Se, Table 5, where any E is O, S or Se;

where D is $D^2$=C— or $\oplus D^2$—C=, Z is any radical set forth in Table 6 or Table 7, where any $E^1$ is N and any E is O or S;

where G, $G^1$ or $G^2$ are independently a substituted or unsubstituted aromatic ring system, the ring system is any diradical set forth in Table 8, and where G, $G^1$ or $G^2$ is a substituted or unsubstituted aromatic heterocyclic ring system, the heterocyclic ring system is any diradical R9 set forth in Table 9, where any $E^1$ is N and any E is O or S;

where R is a substituted or unsubstituted diradical comprising an aromatic carbocyclic ring system, the ring system is any diradical R8 set forth in Table 8, and when R is a substituted or unsubstituted aromatic heterocyclic ring system, the heterocyclic ring system is any diradical R9 set forth in Table 9, where any $E^1$ is N and any E is O or S;

the substituents for any of the substituted ring systems of D, X, Y Z G, $G^1$, $G^2$ and R being any of J, $R^1$, $R^2$, G—$R^3$ or Q; and if $R^1$ or $R^2$ is attached to O, N or S, $R^1$ and $R^2$ are independently H, Q, alkyl of 1 to 22 carbons, cycloalkyl of 3 to 22 carbons, or a substituted or unsubstituted aromatic ring system of 6 to 16 carbons or a substituted or unsubstituted aromatic heterocyclic ring system of 5 to 14 members in the ring system, the members being carbon atoms and 1 to (h—1) heteroatoms, where h is the number of members in the heterocyclic ring system, the heteroatom being one or more of N, P, As, Sb, O, S, Se or Te, the $R^1$ or $R^2$ substituents being j1 or $L^1$ with the proviso that the maximum number of $R^1$ or $R^2$ substituents is 6.

Non-limiting examples of the presently preferred Q groups are:

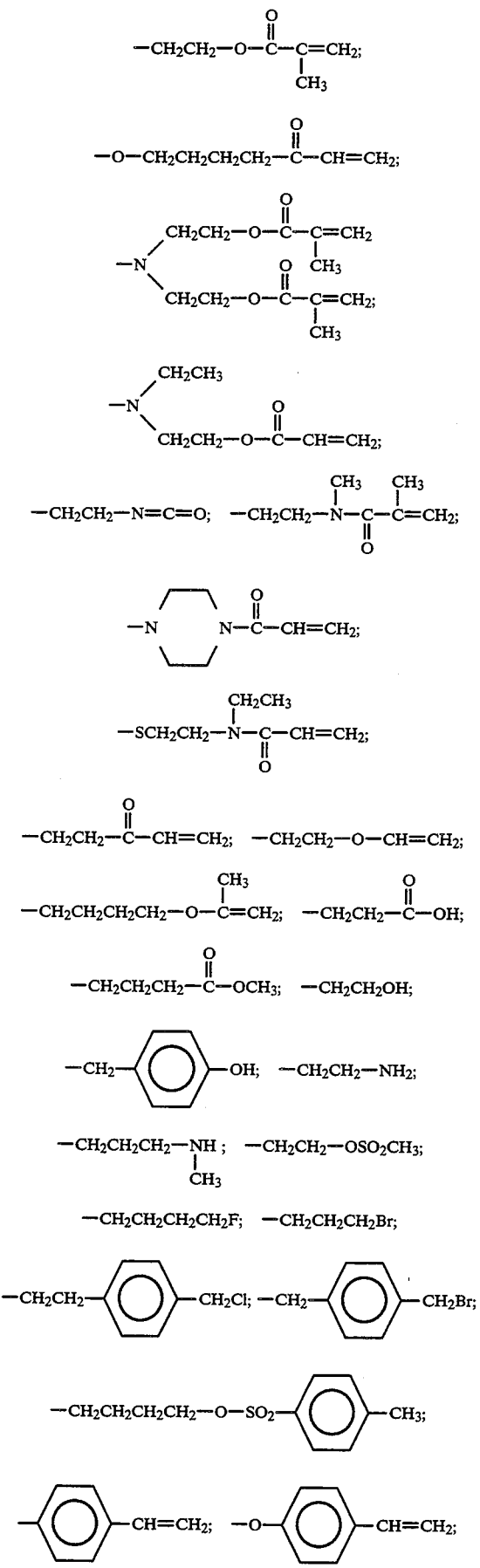

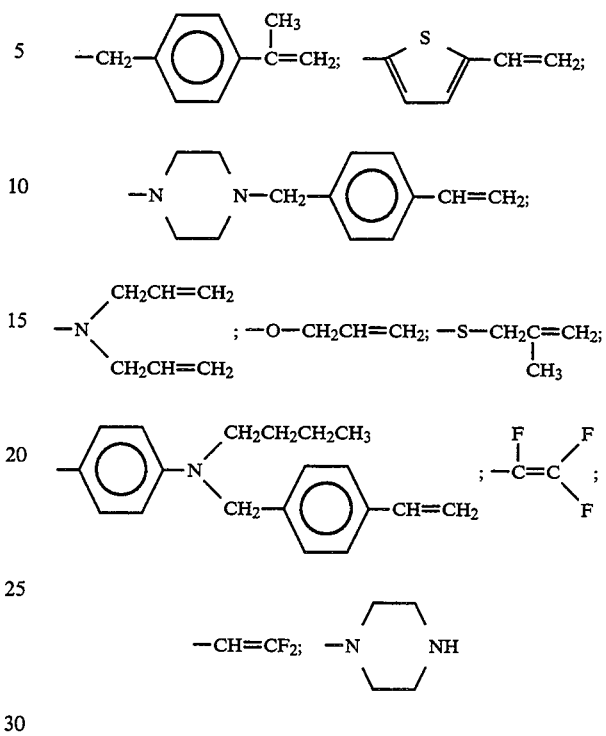

Preparation of Electroactive Compounds

One novel process according to the present invention for making the novel electroactive compounds, where D is $D^1{=}X{-}$ or $\oplus D^1{-}X{=}$, where $D^1$ is any-radical set forth in Table 2, where any $E^1$ is N, P, As or Sb, and $D^1$ is substituted with a J or L group, comprising the following steps:

(a) reacting a starting material having a structure

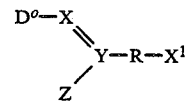

where $D^o$ is any radical set forth in Table 1, where $X^1$ is F, Cl, Br, I or $-OA^2$, and where $A^2$ is an electron withdrawing group independently having the same definition as A or $A^1$, with a carbanion containing an alpha-H atom having a structure

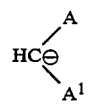

under conditions sufficient to form a heterostilbene carbanion having a structure

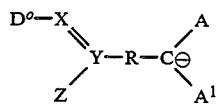

or its corresponding acid form having a structure

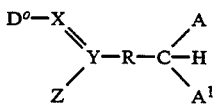

(b) reacting the heterostilbene carbanion of step (a) or its corresponding acid with a compound having an electron donating group J or a withdrawing group L to form a J or L substituted compound having structures

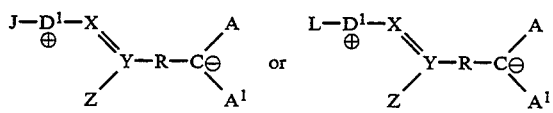

or their corresponding resonance canonical structures

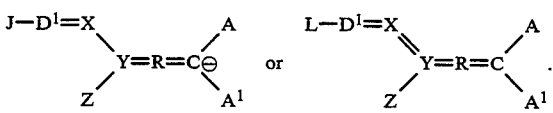

The generalized process requires, as the other and remaining specific generic component, a carbanion disubstituted with electron-withdrawing groups and monosubstituted with a single hydrogen atom:

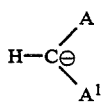

Such carbanions are available by a broad range of methods well known to those skilled in the art, the most common of which is the reaction of a di(acceptor)-substituted methane with a base:

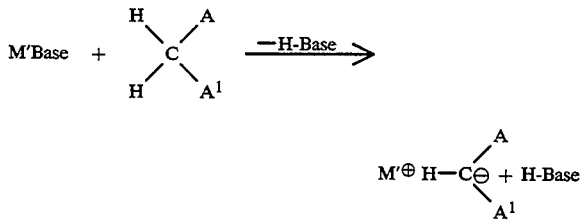

Such bases include amines or guanidines or metallic hydrides, hydroxides, alkyls, alkoxides, amides, phosphides, nitrides, imides, silanes and siloxides as the most preferred class. Preferred solvents include both protic and aprotic solvents. Preferred protic solvents include water; alcohols (1-22 carbons); aralkanols (1-28 carbons); amines (1 to 44 carbons); amides (1-22 carbons); and anilines (6 to 36 carbons). Preferred aprotic solvents include ethers (2 to 44 carbons); esters (2 to 44 carbons); nitriles (2-22 carbons); amides (3 to 36 carbons); sulfoxides (2 to 44 carbons); sulfones (2 to 44 carbons); phosphoramides (6 to 66 carbons); ureas (4 to 88 carbons); carbamates (3 to 66 carbons); amines (3 to 66 carbons); anilines (8 to 50 carbons); alkanes (4 to 22 carbons); arylalkanes (7 to 50 carbons) arenes (6 to 60 carbons); silanes (4 to 88 carbons); cycloalkanes (4 to 44 carbons); aromatic and saturated heterocyclic compounds (1 to 29 carbons); haloalkanes (1 to 44 carbons, 1 to 10 halogens from Cl, F, I, Br); haloureas (1-50 carbons, 1-10 halogens from Cl, F, I, Br); sulfonamides (2 to 44 carbons); dicarboximides (3 to 44 carbons); disulfonimides (3 to 44 carbons); sulfides (2 to 44 carbons); ketones (2-44 carbons); aldehydes (2 to 22 carbons); iraides (2 to 66 carbons); or an excess of the all-(acceptor) substituted methane. In addition, the reaction may be conducted without solvent in a melt of the reactants. Most preferably is the arrangement wherein the formation of the carbanion intermediate and the subsequent reaction are conducted in the same solvent and the same vessel.

The heterostilbene intermediate, prepared in step (a), whether in carbanion or acid form, is believed to be a new compound. Once the method used to make the intermediate compound is known as a result of this invention, modifications to the method of making the intermediate would be well-known to one of ordinary skill in the art. Likewise, once one realizes the desirability of making the electroactive compounds according to the present invention, methods of doing so, based on the novel heterostilbene intermediates, would also be known to those skilled in the art without undue experimentation, based on the present disclosure. Methods of making a carbanion containing an alpha-H atom are so well known that they need not be described in detail herein.

Typically, the heterostilbene intermediate may be prepared by reacting a haloheterostilbene with the carbanion containing at least one alpha-hydrogen atom with various known transition metal catalysts, such as ligated Pd[O], such as ([C$_6$H$_5$]$_3$P)$_4$Pd[O]; ligated Ni[O], such as ([C$_6$H$_5$]$_3$P)$_4$Ni[O]; and ligated Cu[I] such as (CH$_3$CN)$_4$Cu[I]ClO$_4$.

The following two equations represent specific, non-limiting examples of reactions involving a heterostilbene carbanion to make novel electroactive compounds of the present invention. The reaction equations demonstrate that, rather than undergoing carbon-alkylation, for example, when reacting the heterostilbene carbanions with alkyl halides or other leaving groups, the alkylation does not occur at the —C(A)(A$^1$) portion of the molecule, but rather, at the heterocyclic end of the molecule, such that the alkyl or other group bonds to a heteroatom. This reaction was not predicted and expected. However, now that one skilled in the art is made aware of this type of reaction based on the present disclosure, one could readily use this knowledge and general chemical principles to create a great many other electroactive compounds within the scope of this invention.

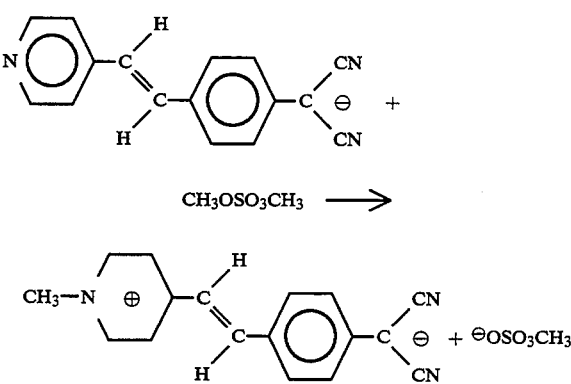

-continued

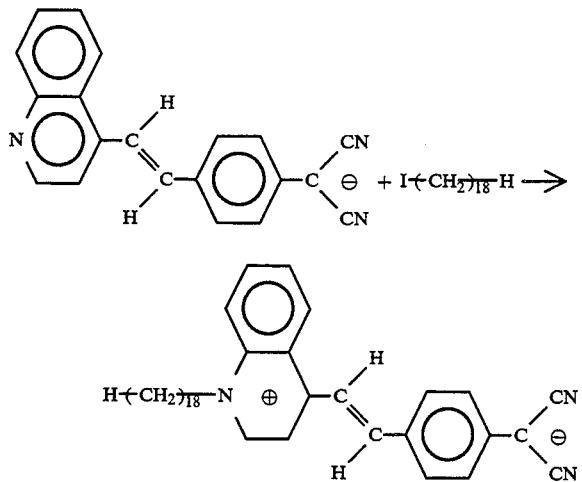

Another the novel process of making an electroactive compound according to the present invention, wherein D is $D^1=X-$ or $\oplus D^1-X=$, comprises the following steps:

(a) reacting a first starting material having a structure

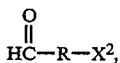

where $X^2$ is a leaving group comprising F, Cl, Br or I or $-OA^2$ where $A^2$ is an electron withdrawing group independently having the same definition as A or $A^1$, with a carbanion containing an alpha-H atom having a structure

under conditions sufficient to form an aldehyde intermediate having a structure

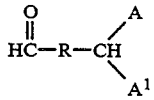

or its corresponding carbanion having a structure

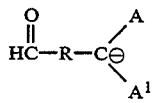

(b) reacting the aldehyde or carbanion intermediate formed in step (a) with a compound having a structure

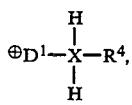

where $R^4$ is a lone electron pair for trivalent X or J, L, $R^1$, $R^2$, $G-R^3$ or $G-Q$ for tetravalent X, under conditions sufficient to form the novel electroactive compounds of the present invention having a structure

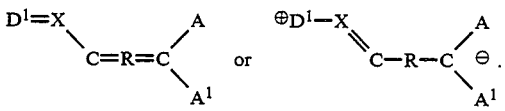

The reaction of step (a) preferably occurs using the transition metal catalysts referred to above where $X^2$ is Cl, Br or I. The reaction occurs directly, where $X^2$ is F or $-OA^2$, in aprotic organic solvents. The step (b) reaction conditions are generally that the reaction take place at temperatures from about 0° C. to about 300° C. in any suitable organic solvent in the presence of a mild Lewis base catalyst, such as ammonia, alkylamine, alkali carbonate, alone or in the presence of a small amount of a mild acid, such as an aromatic carboxylic acid, an aromatic carboxylic acid, a heterocyclic carboxylic acid or a Lewis acid, such as $Zn^2\oplus$, $Mg^2\oplus$, $Li\oplus$. More preferred reaction conditions include the use of excess piperidine with a smaller amount of acetic acid in an alcohol solvent at reflux conditions.

Specific, non-limiting examples of reaction equations involving the aldehyde intermediate are set forth below, with the understanding that one skilled in the art could readily devise many other similar reaction equations involving other starting materials to produce other types of electroactive compounds according to the present invention.

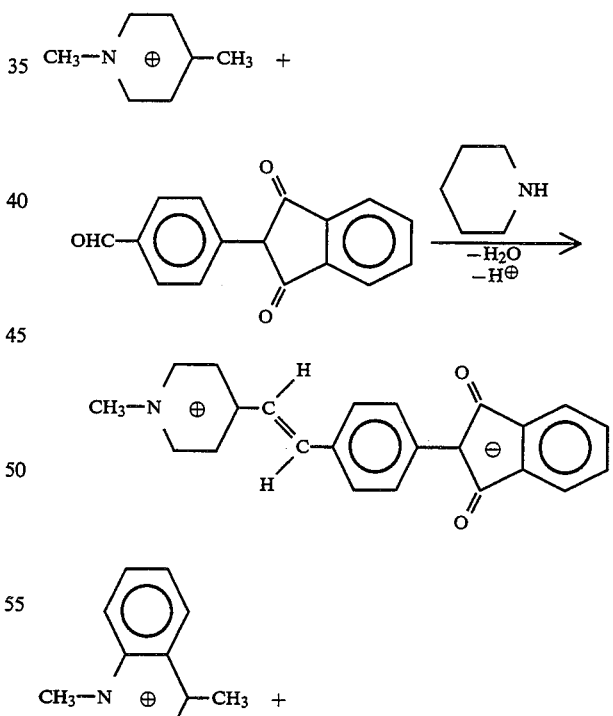

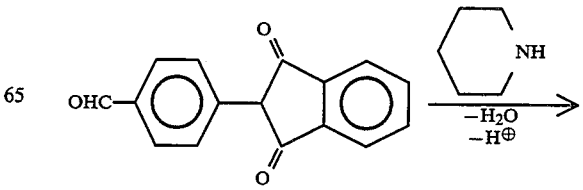

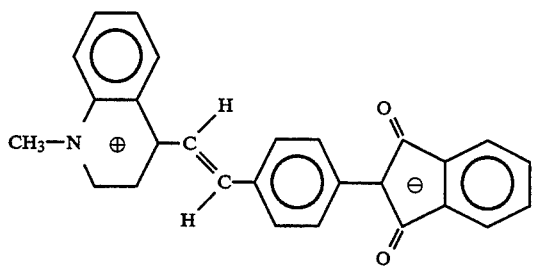

In addition to the method for preparing the novel aldehyde intermediate as set forth in step (a) of the process set forth above, the aldehyde intermediate can be prepared by the following process;

(a') reacting a first starting material having a structure

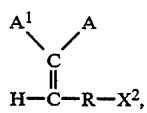

with a carbanion containing an alpha-H atom having a structure

under conditions sufficient to form an intermediate having a structure

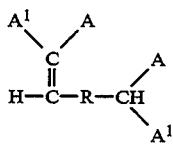

or its corresponding carbanion having a structure

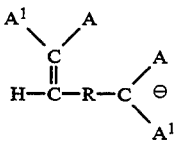

(b') reacting the intermediate of step (a') under conditions of hydrolysis sufficient to form an aldehyde intermediate having a structure

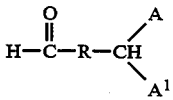

or its corresponding aldehyde carbanion intermediate having a structure

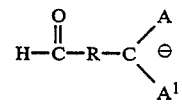

Once the aldehyde intermediate or its corresponding aldehyde carbanion intermediate is formed, the reaction proceeds as set forth in step (b) above to produce the same novel electroactive compound according to the present invention.

Another novel process according to the present invention relates to a process for making a novel electroactive compound wherein D is $D^2$=C— or $\oplus D^2$—C= and Y is C, comprising reacting a starting compound having a structure

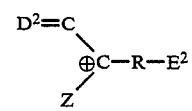

and a resonance canonical structure

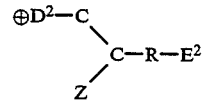

where $E^2$ is a leaving group which can exist as a stable anion $E^2 \oplus$ or when present as H—$E^2$, H—$E^2$ is acidic relative to organic polar aprotic solvents, with a carbanion containing an alpha-H atom having a structure

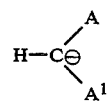

under conditions sufficient to form a novel electroactive compound of the present invention having a structure

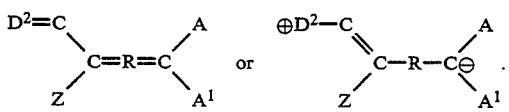

Preferably, $E^2$ is

F, Cl, Br, I, —O—$\overset{\overset{O}{\|}}{\underset{\|}{S}}$—$R^1$, —O—$C_6H_5$—$R^1$, —O—$(CH_2)_n$—H,

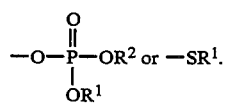

The reaction preferably takes place in an aprotic organic solvent at a temperature of about 0° C. to about 300° C. for up to 100 hours, preferably 1 to 10 hours. It is also preferred that the reaction take place in an excess of the carbanion or in the presence of a mild aprotic base, such as a tertiary amine.

a. Properties of the Novel Electroactive Compounds

Changes in light absorption due to an applied electric field result in effects called electroabsorption or electrochromism effects. These effects are exhibited by the electroactive compounds of the present invention as demonstrated by the observation of extraordinary shifts of the absorption spectra of the molecules in aprotic solvents of differing polarity, such as tetrahydrofuran (THF) or dimethylsulfoxide (DMSO).

Figure 2:
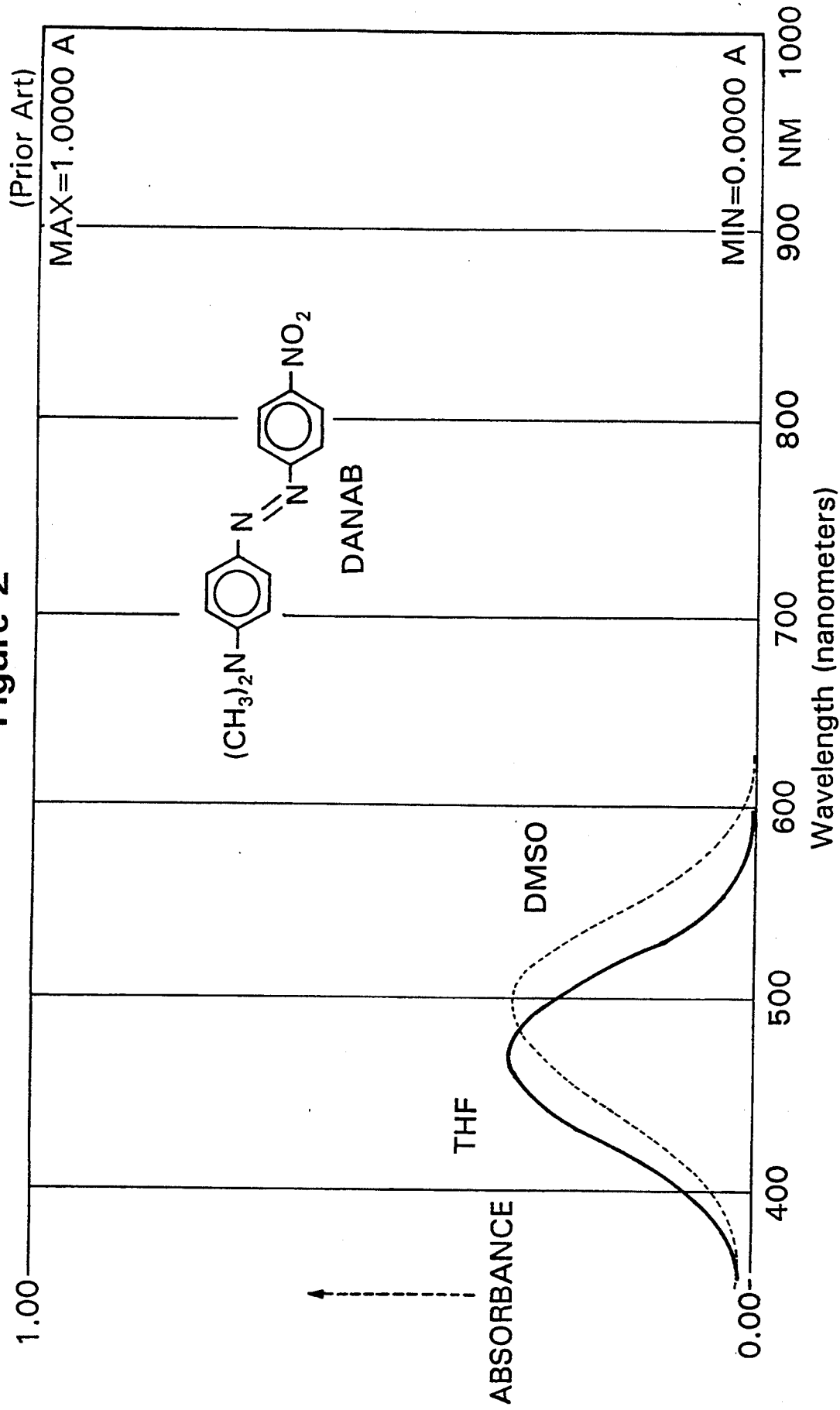
FIG. 2 is an absorption spectrogram indicating the solvatochromism exhibited by the prior art electroactive compound 4-(N,N-dimethylamino)-4'-nitroazobenzene (DANAB).

FIGS. 1 through 5 are absorption spectrograms indicating the solvatochromism exhibited by various electroactive compounds in two solvents of greatly differing polarity. FIGS. 1 and 2 represent the solvatochromism of two known prior art electroactive compounds, 4-(N,N-dimethylamino)-4'-nitrostilbene (DANS) and 4-(N,N-dimethylamino)-4'-nitroazobenzene (DANAB), respectively. The solvatochromism of three exemplary electroactive compounds of the present invention is presented in the spectragrams of FIGS. 3 through 5, wherein a structure of each of the novel compounds is indicated in the Figure.

The absolute difference between the wavelengths corresponding to the absorption maximum of the compounds as determined in the two different solvents represents the magnitude of the solvatochromism. The relative efficacy, that is, the degree of electroabsorption, of the novel compounds can be inferred by comparison of the magnitude of solvatochromism indicated in FIGS. 3 through 5 to that of DANS or DANAB as indicated in FIGS. 1 and 2. All of the conditions relating to the determination of solvatochromism in FIGS. 1 through 5 were identical. All spectra shown in the FIGS. 1 through 5 were conducted on solutions of $1.00 \times 10^{-5}$ molar concentration at an optical pathlength of 1.00 cm and in very high purity, water-free THF and DMSO, respectively. The abscissa of the spectra is the wavelength of the absorbed radiation in nanometers (nm), and the ordinate is in absorbance units ranging from 0.00 to 1.00, on a logarithmic scale. The absorption spectra in THF is represented by a dark, thick, continuous line, while the absorption spectra in DMSO is represented by a light, thin dashed line.

Figure 3:
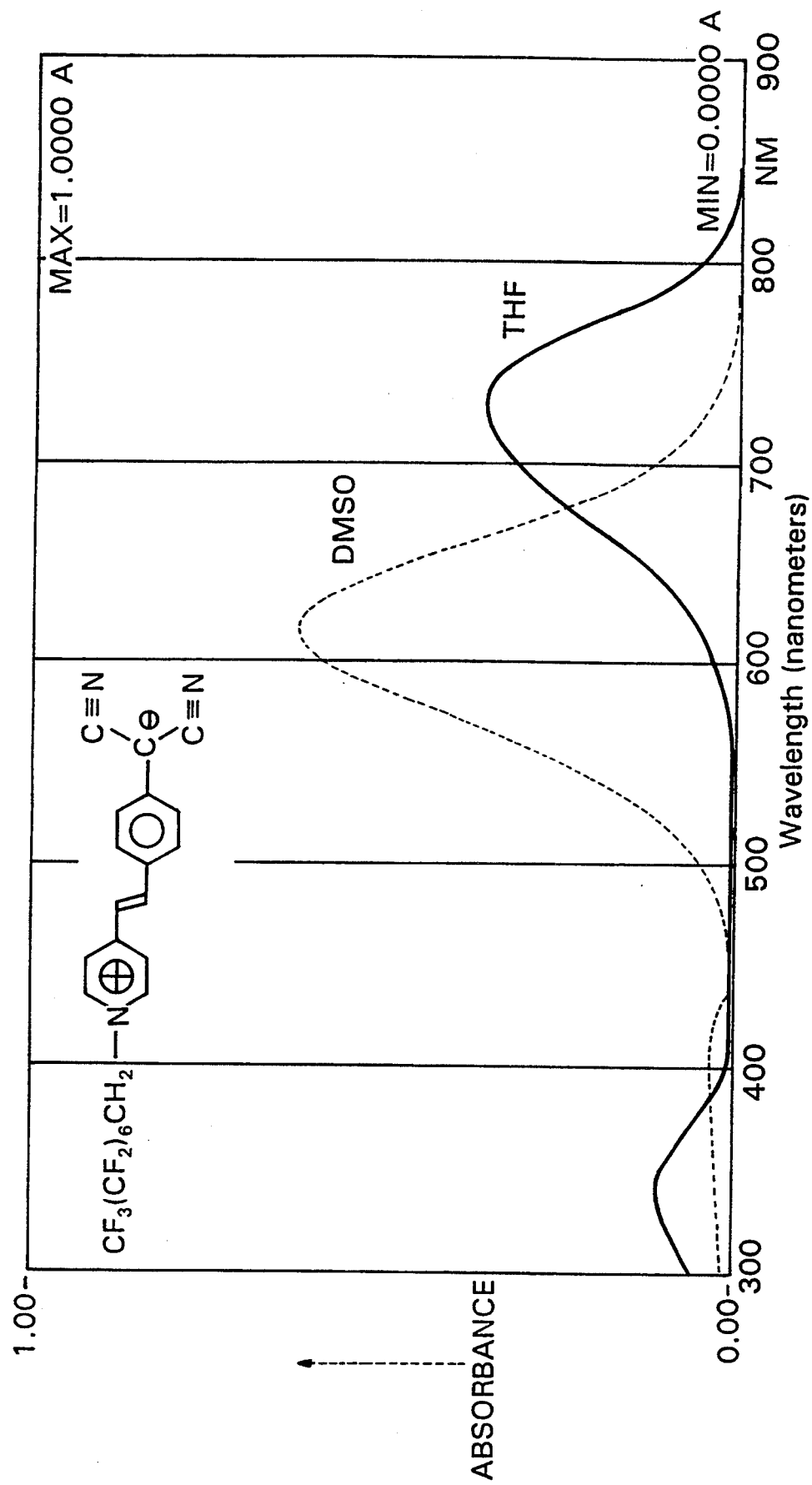
FIGS. 3 through 5 are absorption spectrograms indicating the solvatochromism exhibited by exemplary electroactive compounds of the present invention whose structure is indicated in the Figure.
Figure 4:
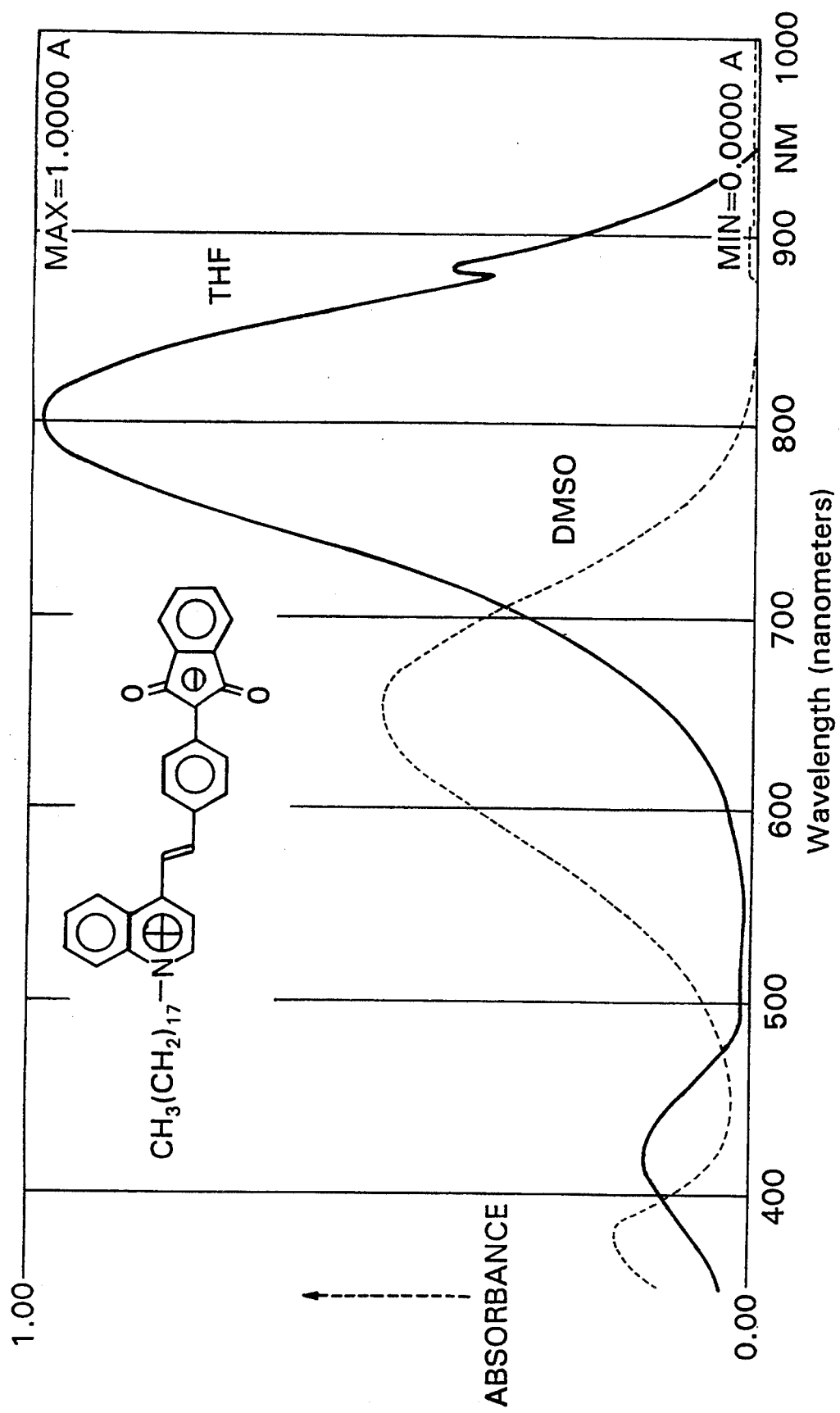
Figure 5:
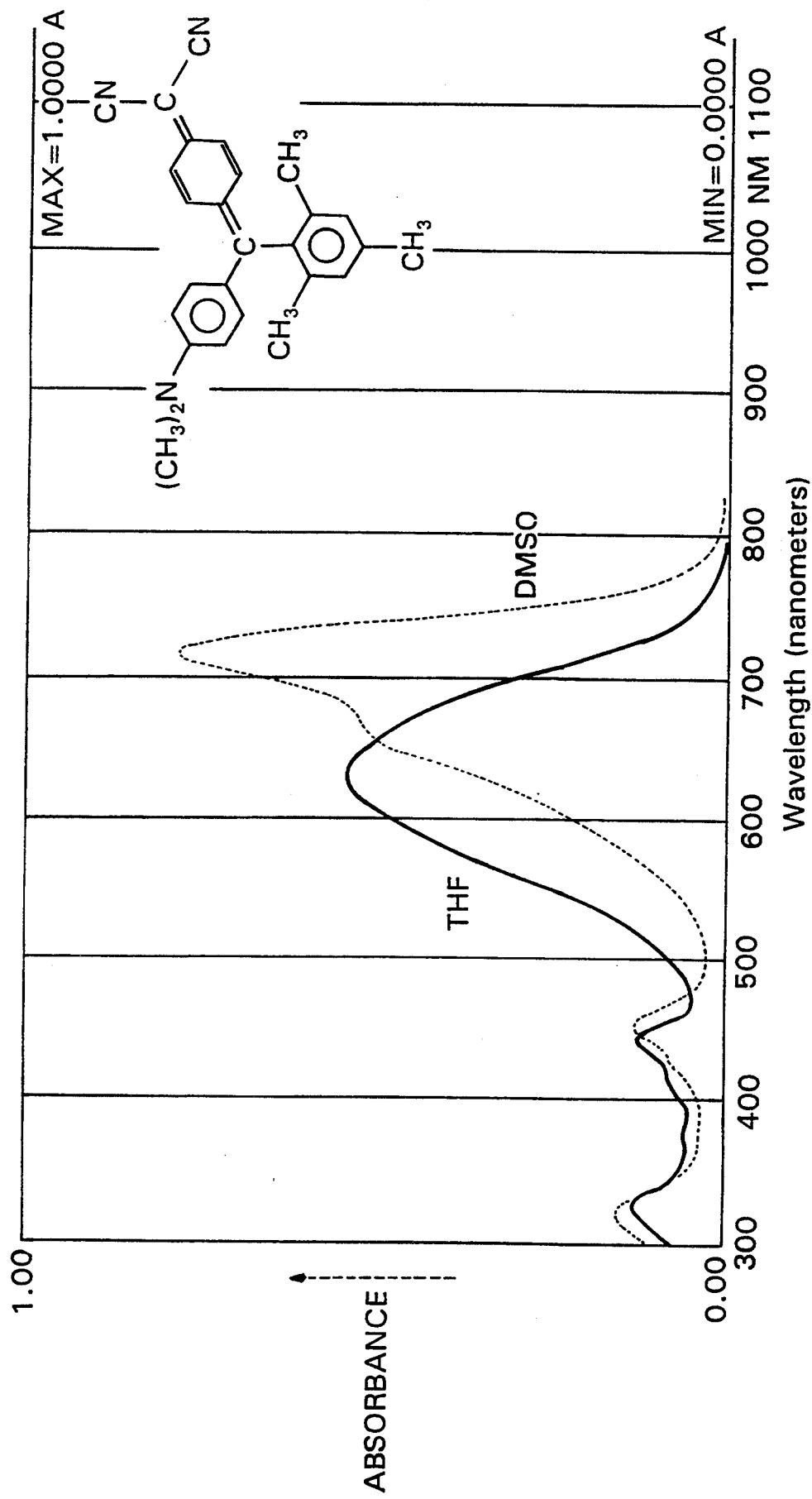

FIGS. 3 through 5 indicate that the novel electroactive compounds of the present invention exhibited solvatochromism of magnitudes 4 to 6 times those of DANS or DANAB. The solvatochromism magnitudes are: 20 nm for DANS in FIG. 1; 24 nm for DANAB in FIG. 2; 113 nm for the novel compound in FIG. 3; 149 nm for the novel compound in FIG. 4; and 86 run for the novel compound in FIG. 5.

When the electroactive compounds of the present invention are incorporated in various compositions, typically polymers, as well as other materials, all as described hereinafter, the material containing the electroactive compound will itself be electroactive due to its ability to absorb or refract light. As used herein, the term "light" means any wavelength of light in the electromagnetic spectrum capable of being transmitted by and through electrooptical devices and components, such as optical fibers, whether or not such light is in the visible spectrum range. Typically, light having a wavelength between about 800 nm and about 2,000 rnn is readily transmittable using state of the art light emitting diodes (LED) and laser diodes. More particularly preferred are electroactive compounds and materials absorbing light within the wavelengths of about 850 nm, 1300 nm and about 1,550 nm.

Because electroactive compositions and materials according to the present invention absorb certain wavelengths of light when they become electroactive in the presence of a static electric field, the materials have the ability to pulse or modulate the intensity of a light ray passing through the material. Increased absorption when an electric field is applied will decrease the intensity of the transmitted light, while decreased absorption will permit an increase in light transmission.

The electroactive compounds and compositions of the present invention also undergo changes in light refraction due to an applied electric field. Such changes in light refraction are due to effects variously termed the electrooptical effect, the Kerr effect, or electric field induced birefringence. The electrooptical effect can also confer upon a material containing the compounds of the present invention the ability to modulate light intensity when applied in a system which uses polarized light and polarizing optics or interferometric optics. A field induced by birefringent sample of material placed between two light polarizers in parallel orientation will pass polarized light if the applied field is off and prevent passage if the field is on. Conversely, if the two light polarizers are offset to prevent light passage when the field is off, light transmission will be permitted when the field is turned on. Similarly, light modulation is possible by application of a phase-sensitive interferometer, such as a Mach-Zehnder interferometer, a Franz-Keldysh modulator, as well as multichannel modulators. These electrooptical components are readily constructed using techniques well known to those skilled in the art.

The electroactive compounds of the present invention also have a unique property of undergoing a permanent change in refraction upon exposure to certain, well-defined bands or wavelengths of optical radiation. This is a particularly novel phenomonen associated with the electroactive compounds of the present invention. This property permits the use of a photolithographic-type of process to generate electroactive optical waveguides made from materials containing the novel electroactive compounds. A typical photolithographic-type of process for making electroactive optical waveguides will be described hereinafter. Generally, an absorption band in the region of 250 nm to 550 nm can be irradiated in the compounds of this invention to effect the permanent refraction change.

Electroactive Compositions

Electroactive compositions can be prepared based on the present invention by incorporating the novel electroactive compounds into various matrix materials, such as liquids, liquid crystals, polymeric materials or crystals. In each instance where the electroactive compounds are incorporated in a matrix, the molecules of the novel compounds must be oriented such that their electric moments are aligned in the same direction so as to be polarized or anisotropic. By virtue of their level of electric polarization, based on their large dipole moment, the molecules of the electroactive compounds of the present invention will become highly oriented in solutions in the presence of low electric fields on the order of about 0.1 kv/cm to about 10 kv/cm. Under these conditions, low frequency (less than or equal to about 100 khz) optical modulation, since orientation of the molecules is accompanied by dichromism and by birefringence. When the molecules of the compound of the present invention are in aprotic solvent between positive and negative electrodes, the dipole of the molecules will be oriented contrapolar to the polarization of the electrodes. In such an oriented mode, the resulting solution containing the oriented molecules will be capable of inducing high intensity (greater than about 1 MW/cm$^2$) coherent light to undergo frequency doubling. This property is of considerable utility in generating coherent light at wavelengths which are not easily achieved with currently available lasers. The property of frequency doubling influenced by an electric field is known as EFISH (electric field induced second harmonic) due to the high first order hyperpolarizability (beta) exhibited by the compounds of the present invention.

If the magnitude of the applied electric field is considerably increased (on the order of about 1 MV/cm), the novel molecules will undergo an increase in their dipole moment due to the high intrinsic distortion polarizability (alpha) of the compounds. The more highly polarized or hyperpolarized molecules will exhibit different optical absorption spectra and birefringence than the materials in a lower electric field. Therefore solutions will be capable of effecting optical modulation by electroabsorption or electrooptical mechanisms.

Although molecules of the novel compounds can be oriented at moderate electric field strengths and fluids, the desired molecular orientation can be achieved at considerably lower fields if a matrix in which the compound is incorporated is a liquid crystal. Orientation may also be achieved in this type of matrix without any use of an electric field by use of mechanical processes, such as stretching or compression. If desired, compression or stretching in combination with an electric field could be used to enhance orientation of the molecules.

Compositions

The preferred liquid crystal molecules are nematic liquid crystals of a type well known to those skilled in the art. See, for example, G. W. Gray, *Molecular Structure and the Properties of Liquid Crystals*, Academic Press, New York, N.Y. (1962); H. Kelker and R. Hatz, *Handbook of Liquid Crystals*, Verlag Chemie, Weinheim, Germany (1980); and A. Ciferri, W. R. Krigbaum and R. B. Meyer, *Polymer Liquid Crystals*, Academic Press, New York, N.Y. (1982).

A nematic liquid crystal is comprised of highly elongated molecules which are aligned in one direction in the nematic phase. Nematic order may be induced or extended by appropriate application of electric field, compression or stretching forces. Nematic liquid crystal systems are orientable at very low electric fields on the order of about 10 V/cm to about 1 kv/cm or by simple application of compression or stretching forces. Once the molecules of the present invention are aligned in nematic liquid crystal, application of very high fields on the order of higher fields on the order of about 10 kv/cm to about 10 MV/cm may be applied to effect electrooptical or electroabsorption modulation when hyperpolarized molecules are produced in the nematic liquid crystal matrix.

Compositions of the present invention comprising the novel electroactive compounds in liquid crystal matrices are capable of modulating light in two different mechanisms operating in two different electric field or applied voltage ranges. At low electric fields (less than about 10$^5$ V/cm, the compositions act as a dichroic modulator by virtue of their high dipole moment and elongated molecular structure. At high electric fields (greater than about 10$^5$ V/cm), the electroactive compositions modulate light by electrooptical or electroabsorbance mechanisms as a result of their high polarizability (alpha) and first order hyperpolarizability (beta).

The preferred matrix into which the electroactive compounds of the invention are incorporated to make electroactive compositions are polymeric matrices. The compounds can be dissolved in a polymeric matrix and subjected to strong electric field as the composite is melted and cooled to normal temperatures to retain the molecules of the electroactive compounds in field-induced alignment which will be maintained within the rigid amorphous regions of the polymer. Similarly, the desired orientation can be obtained by polymerizing a crosslinked polymer containing the electroactive compounds in the presence of an electric field. Improved levels of orientation can also be achieved by compression or stretching during a heating-cooling cycle, with even better orientation achievable when compression or stretching is combined with the application of an electric field.

The preferred polymeric matrix material is poly(vinylidene fluoride); a copolymer of vinylidene difluoride with hexafluoropropylene, trifluoroethylene or tetrafluoroethylene; a terpolymer of vinylidene difluoride or vinylidene trifluoride with tetrafluoroethylene and hexafluoropropylene; a terpolymer of a vinylic monomer, acrylic monomer or methacrylic monomer with tetrafluoroethylene and hexafluoropropylene; a copolymer of vinylidene difluoride and acrylic ester, methacrylic ester or acrylamide; or a tetrapolymer of vinylidene difluoride, vinylidene trifluoride, tetrafluoroethylene and hexafluoropropylene.

It is presently preferred that the electroactive compounds be incorporated into a matrix to make a composition by including about i to about 10% of the compounds in the matrix material. This general concentration applies regardless of the type of matrix involved and regardless of whether the electroactive compound is used in a solvent system, blended in a melt or becomes covalently bonded to the polymeric matrix. Although the polymeric matrix may be a homopolymer, it is presently preferred that the matrix be a copolymer, terpolymer or tetrapolymer of the various monomers referred to above.

Polymeric matrices including poly(vinylidene fluoride), in which the vinylidene fluoride monomer is preferably referred to as vinylidene difluoride, are preferred, since the poly(vinylidene fluoride), when highly oriented by longitudinal stretching, possesses a highly stable nematic liquid crystal structure. Highly polar and complex polycyclic organic molecules can be firmly oriented in a specific manner within the nematic liquid crystalline polymeric structures. Such materials have very good stability over a broad temperature range and over a long time period. However, polyvinylidene fluoride homopolymer is not ideal as a matrix for an electroactive composition of the present invention, since it is a cloudy material which scatters light. The light scattering can be substantially eliminated if the vinylidene fluoride is combined with other monomers, and particularly fluorinated monomers. When tetrafluoroethylene is added to vinylidene difluoride, the light scattering is substantially eliminated. Clarity is improved even further upon a further addition of hexafluoropropylene. Thus, terpolymers of vinylidene difluoride, tetrafluoroethylene and hexafluropropylene are the presently preferred monomers for making a polymeric matrix containing the electroactive compounds of the present invention.

The vinylidene difluoride component should be present in an amount greater than 50%, preferably in the range of about 85% to about 99%, to provide the ordered nematic liquid crystalline regions and the high level of dimensional stability to orient the molecules of the electroactive compounds of the present invention following polling and/or physical orientation. While terpolymers containing a broad range of vinylic or acrylic monomers should be able to be used effectively, the use of tetrafluoroethylene and hexafluoropropylene (and to some extent, the acrylic monomers) help prevent the formation of large crystals of vinylidene difluoride which scatter electromagnetic radiation in the ultraviolet, visible and near infrared regions. It is presently preferred that the tetrafluoroethylene component be present in the range of about 0.5% to about 49.5%, and most preferably, in a range of about 5% to about 40%. It is presently preferred that the terpolymer also contain hexafluoropropylene in a range of about 0.1% to about 25%, with the presently more preferred range of about 0.5% to about 10%.

polymers. The electroactive compounds can be incorporated either as pendant groups or into the backbone of the polymer. One technique for making polymers in which the electroactive compound is a pendant functional group employs the reaction of a monomer-alkylating agent which reacts with a composition of the present invention in a carbanion form, resulting in the formation of an electroactive monomer. The electroactive monomer is then polymerized using free radical initiation or anionic initiation, resulting in an addition polymer. The following reactions provide a specific, non-limiting illustration of these techniques. The reactions are intended to illustrate the general reaction schemes and the principles may be applied to other starting materials and monomers as would be recognized readily by those of ordinary skill in the art.

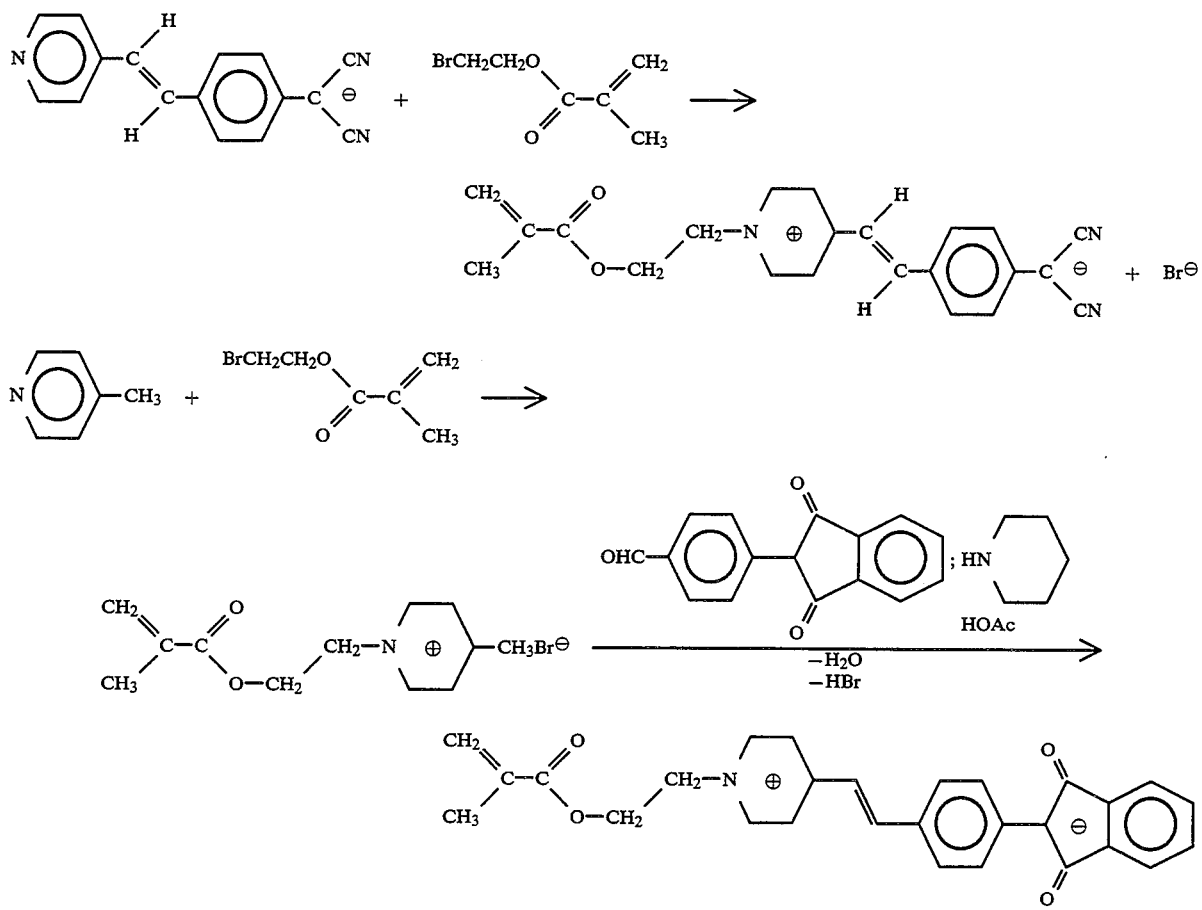

Polymer-Bound Electroactive Matrices

As indicated above, although the electroactive compounds of the present invention can be added to a polymeric matrix by merely blending the components together, it is presently preferred that the electroactive compounds of the present invention be incorporated into the molecular structure of the polymers as functional groups, thus creating electroactive functional The resulting monomers are examples of acrylic or vinylic types of monomers. By application of alkylating condensation monomers, condensation polymers as set forth below can be created easily using chemistry well known to those skilled in the art based on the present disclosures. For the sake of simplicity, monomers having the following schematic or diagrammatic structure 2 will be used:

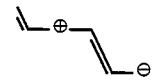

2

Using the simplified schematic structure 2, to signify an electroactive monomer according to the present invention, the following condensation polymers will result, wherein m and n are each independently an integer of 1 to 22, for example. An addition polymer 3 or 4:

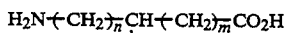  3

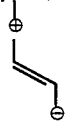

  4

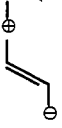

Polymerization of monomer 2 using a free radical or anionic initiator will result in the formation of an addition polymer 5 as follows. Similarly, thermal polymerization of monomer 3 will result in condensation polymer 6. Catalyzed elimination of ethanol from monomer 4 will result in polyester 7 as follows:

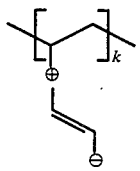  5

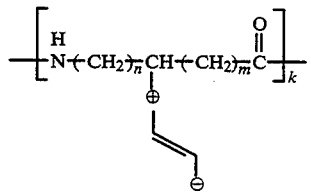  6

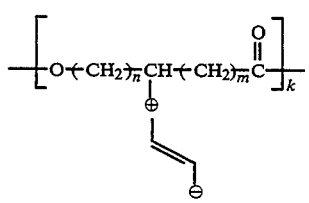  7

In each of the polymers 5, 6 and 7, k indicates generally the degree of polymerization.

Pendant polymers in which the electroactive compounds of the present invention are pendant functional groups in a polymer may also result from reactions using various nucleophilic groups. Thus, for example, a heterostilbene carbanion or a 4-picoline are broadly representative of nucleophiles which may be reacted with an alkylating polymer, such as poly(2-bromoethyl methacrylate). Polymers with pendant electroactive functional groups can be prepared as indicated in the following specific, non-limiting examples of suitable reactions schemes.

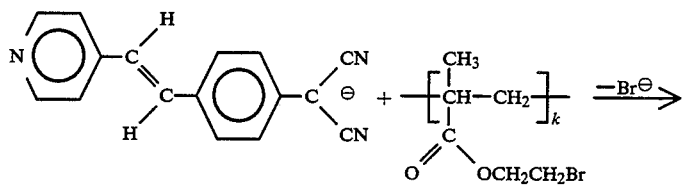

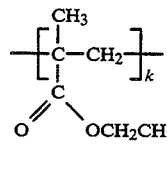

8

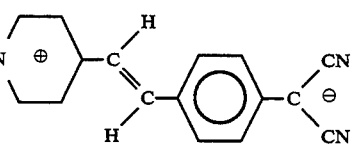

9

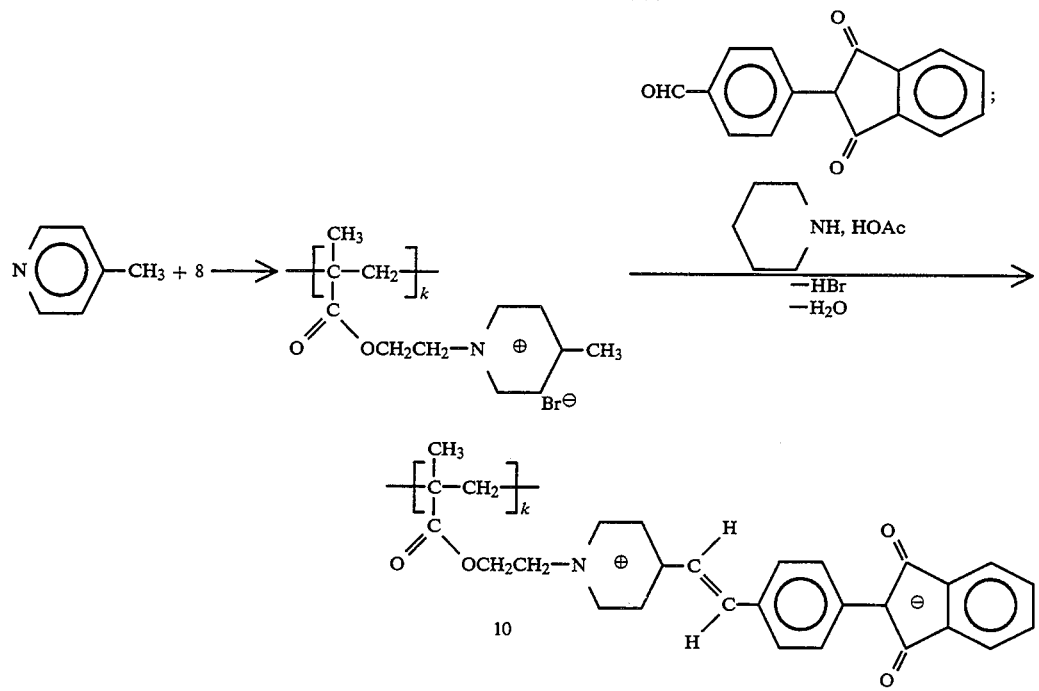
Nucleophiles such as the heterostilbene carbanion and 4-picoline may react with bis-alkylating agents, such as 2-bromoethyl methanesulfonate to generate electroactive alkylators 11 and 12 in the following specific, non-limiting examples of reactions:
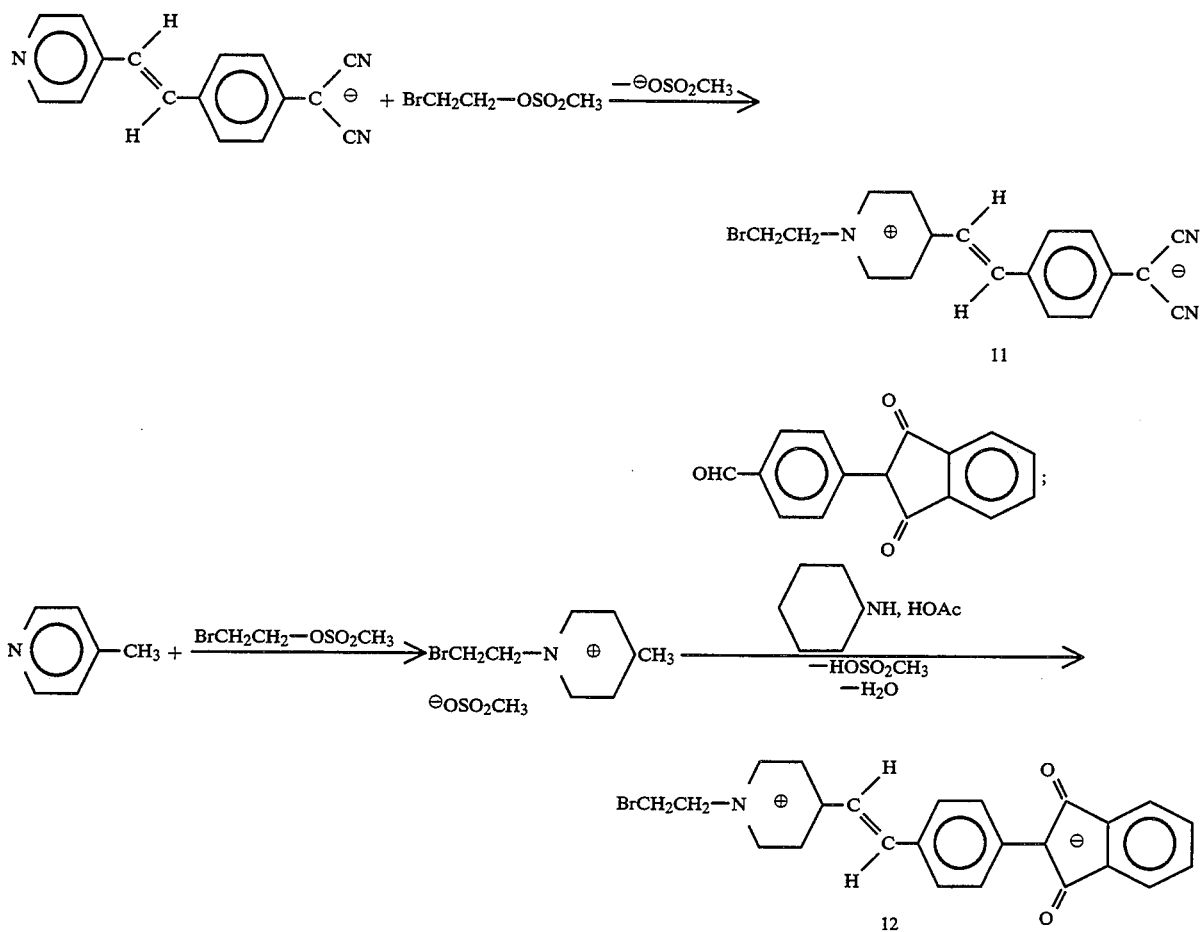

Reaction of the electroactive-alkylators 11 and 12 with silver poly(methacrylate) will generate electroactive functional polymers 9 and 10, respectively, wherein 9 and 10 are set forth above. In this scheme, the electroactive alkylators 11 and 12 function as electroactive electrophiles.

Through the use of electroactive-monomers, electroactive-nucleophiles and electroactive-electrophiles, electroactive pendant homopolymers can be created as described above. Clearly, by using the appropriate comonomer or ensemble of comonomers, spacer monomers can be provided between the electroactive pendant functional groups. Non-limiting examples of such copolymers are set forth below as 13, 14 and 15 in which $M^5$ is defined as below, q is an integer from 1 to 22, for example, and p is the degree of polymerization.

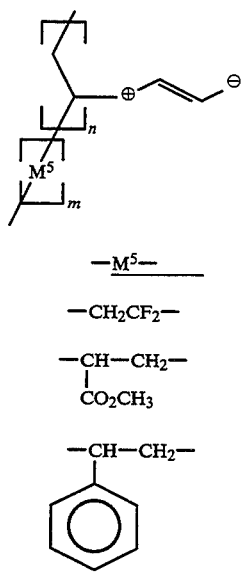

13

—$M^5$—

—$CH_2CF_2$—

—CH—$CH_2$—
    |
    $CO_2CH_3$

—CH—$CH_2$—
    |
    (phenyl)

-continued
—$CF_2CF_2$— etc.

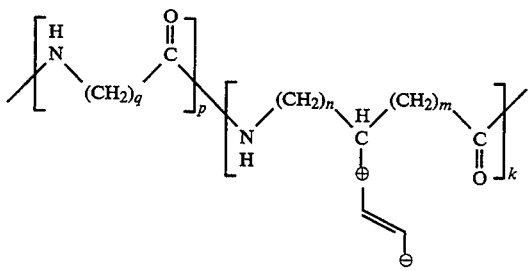

14

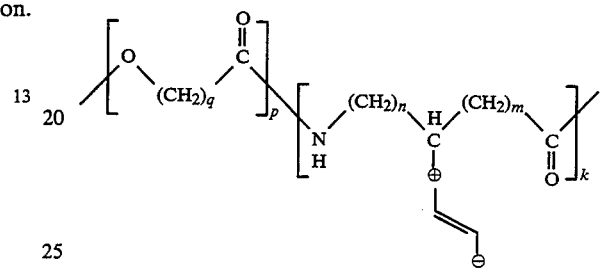

15

As mentioned above, electroactive polymers can be created in which the electroactive functional group is part of the backbone of the polymers. The compounds of the present invention include electron acceptor functions A and $A^1$. Many A or $A^1$ groups possess substituents which permit the elaboration of functionality which are conducive to polymerization, for example, —OH, —$NH_2$, C(=O)OH or the various polymeric groups within the definition of "Q" or groups including "Q". As shown in the reaction schemes above, one may readily synthesize electroactive functional monomers using the techniques described herein in combination with known process chemistry. Additional examples of novel electroactive condensation monomers 16 and 17 may be prepared as typified by the specific, non-limiting reaction schemes below.

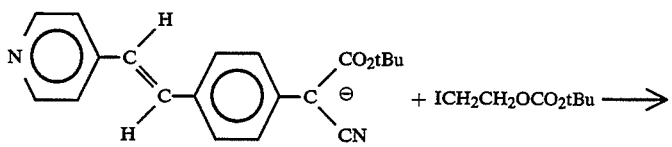

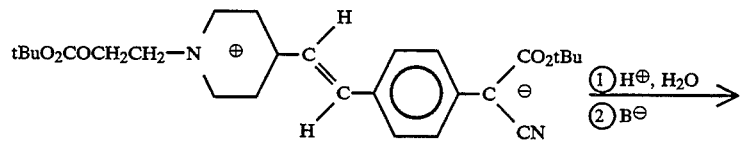

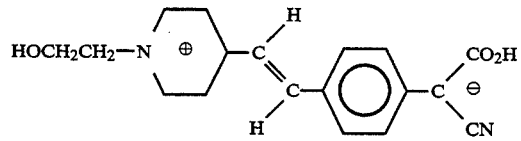

16

-continued

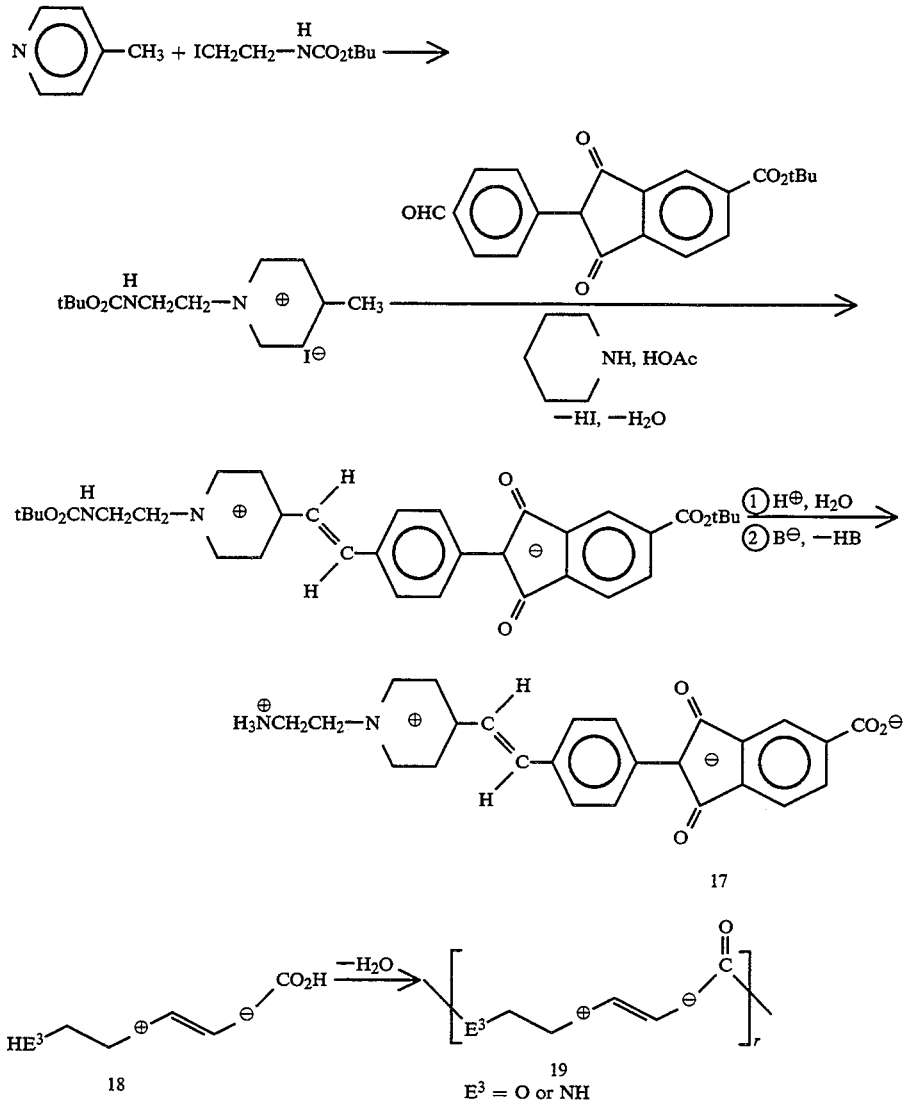

The bifunctional monomeric intermediates 16 and 17 may be viewed as condensation monomers of general structure 18, as follows: polycondensation with the elimination of water will transform the electroactive condensation monomers into electroactive polymers in which the electroactive functional groups are in the backbone, as set forth below with respect to polymer 19, for example. In structures 18 and 19, $E^3$ is O or NH, for example. In polymer structure 19, r is the degree of polymerization.

The electroactive compositions made using the electroactive compounds of the present invention can be used in a host of electrooptical components. The electrooptical components, in turn, may be used to make a host of electrooptical devices for modulating light through light fiber systems, etc.

Although the electroactive compounds of the present invention have their primary and most important use in modulating light as described herein, they may be used in a most basic sense as colorants for compositions containing them. Thus, the electroactive colorants of the present invention typically provide very good and stable coloration to compositions in which they are incorporated, and therefore, they also serve as dyes.

The utility of the compounds, compositions, electrooptical components and electrooptical devices according to the present invention will now be described with reference to FIGS. 6 through 9 and 10a, 10b, 10c and 10d.

Figure 6:
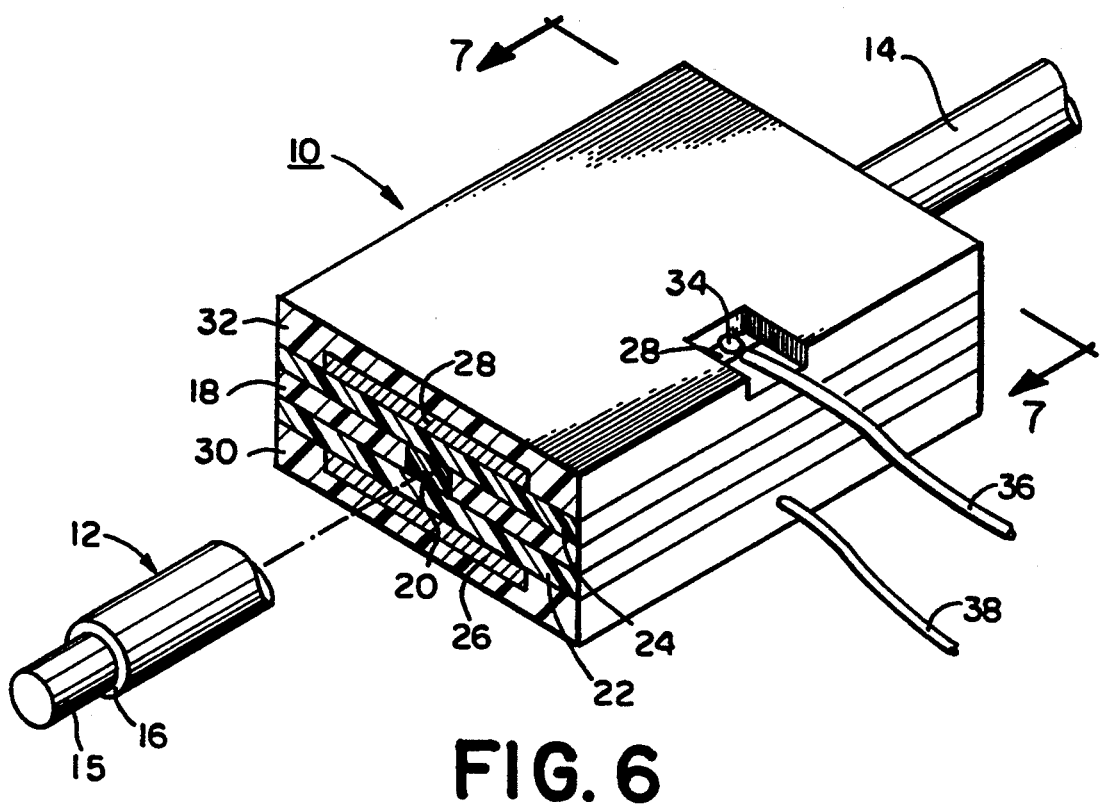
FIG. 6 is a view partly in perspective and partly in vertical section of an embodiment of one type of electrooptical device for modulating light passing through optical fibers, in which the device is constructed using compounds and compositions according to the present invention.

FIG. 6 is a rather diagrammatic illustration, on an extremely enlarged scale, of an electroactive device comprising an electroactive component 10 in accordance with the present invention. Component 10 is adapted to be connected as described below to optical fibers 12 and 14. For purposes of illustration, optical fiber 12 may be an inlet fiber and optical fiber 14 may be an outlet fiber. This means that light enters electrooptical component 10 through optical fiber 12 and exits the component through optical fiber 14. The optical fibers typically include an optical fiber core 15 and a cladding 16 and typically are made of glass, although the optical fibers may also be made of, acrylic or methacrylic polymers or copolymers.

Electrooptical component 10 comprises a core 18 which comprises an electroactive composition. The electroactive composition preferably is a terpolymer of vinylidene difluoride, tetrafluoropropylene and hexafluoropropylene containing the electroactive compound of the present invention either as an additive or, preferably, as polymer bond functional groups. The molecules of the electroactive compound in core 18 have been polled and polarized as set forth above such that their long axes are in alignment and their electric moments are oriented in the same direction and perpendicular to the direction of propagation of the light beam.

Core 18 includes a waveguide 20 preferably made in the manner to be described with respect to FIGS. 10a through 10d below. In essence, core 18 itself can be considered a separate electrooptical component which is part of the larger component 10. As explained below, waveguide 20 has a higher index of refraction than the adjacent portions of core 18, even though core 18 and 20 are made from the same electroactive material, since the adjacent portions of core 18 surrounding waveguide 20 have been irradiated with light of a wavelength which caused the adjacent portions of core 18 to permanently undergo a permanent decrease in refraction. Layers 22 and 24 are cladding layers overlying opposed portions of waveguide 20, but not end faces of the waveguide to which the optical fibers are to be connected. The cladding layers prevent light leakage beyond the waveguide.

Figure 7:
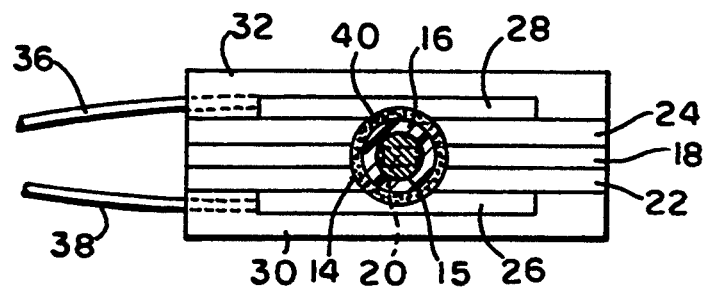
FIG. 7 is an end elevation view, partially in section, of the optical device of FIG. 6 taken along lines 7—7 of FIG. 6.

In the embodiment of component 10 illustrated in FIGS. 6 and 7, electrodes 26 and 28 are also disposed on opposite sides of waveguide 20 such that the electric force field extends transversely through waveguide 20. Electrode 26 may be a negative electrode, while electrode 28 may be a positive electrode. In that case, the electric field effector would extend from positive electrode 28 through the waveguide to negative electrode 26. The electrodes may be extremely thin layers of metal, such as chromium, nickel, an alloy of chromium and nickel, aluminum, silver, gold, platinum and copper, among others well known to those skilled in the art. Chromium, nickel and chromium-nickel alloys are most preferred. The electrodes may be applied using standard photolithographic techniques, electrodeposition, sputtering or other suitable techniques well documented in the literature and known to those skilled in the art.

Layers 30 and 32 illustrated in FIGS. 6 and 7 are encapsulating layers. Although the side edges of all of the layers of component 10 are illustrated in FIGS. 6 and 7 as being flush with each other, encapsulating layers 30 or 32 could extend around the whole component. Likewise, the entire component 10 may be further encapsulated within or otherwise contained in the components of an electrooptical device. The electrodes are energized by current passing through wires 36 and 38 which are attached by solder 34 or other suitable attachment technique.

FIG. 7 is a view of FIG. 6 along lines 7—7 of FIG. 6. FIG. 7 illustrates the attachment of optical fiber 14 to component 10. Optical fiber core 15 is aligned with the end face of waveguide 20 and then the optical fiber is adhesively bonded to component 10 by an optical grade adhesive 40. Suitable optical grade adhesives include, for example, optical grade epoxies curable at room temperature or on gentle heating, or optical grade acrylics, typically containing ultraviolet or visible light sensitizers. The sensitizers cause the curing of the adhesive between fiber and component by a short irradiation with the appropriate wavelength of light. Suitable optical grade adhesives are available commercially and should be selected and have an index of refraction when cured to match that of either the fiber core or the waveguide, or preferably, to be between the indices of refraction of the fiber core and waveguide in value. Optionally, a microoptical device, such as a ball lens or grin (gradient index) lens, can be placed between the fiber core and the waveguide and held in place with the adhesive.

Figure 8:
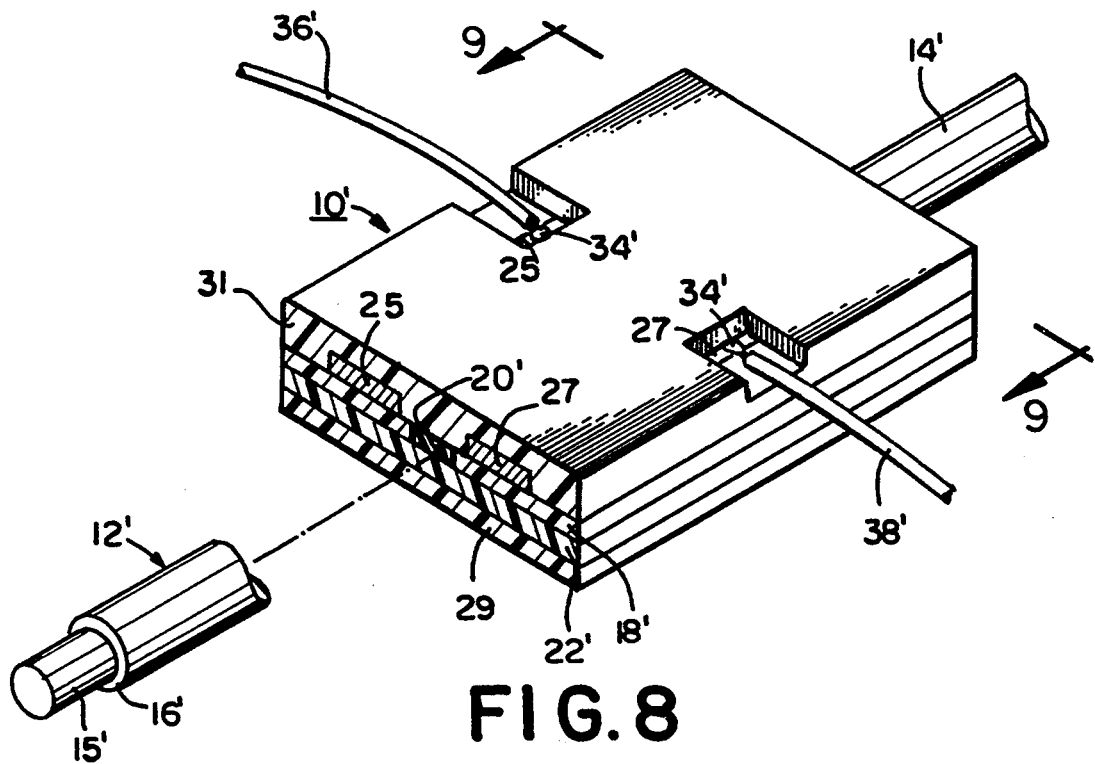
FIG. 8 is a view partly in perspective and partly in vertical section of an embodiment of one type of electrooptical device for modulating light passing through optical fibers, in which the device is constructed using compounds and compositions according to the present invention.
Figure 9:
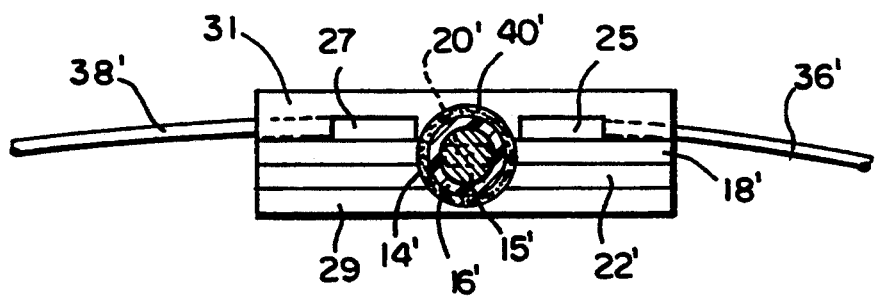
FIG. 9 is an end elevation view, partially in section, of the optical device of FIG. 8 taken along lines 9—9 of FIG. 8.

FIGS. 8 and 9 illustrate an alternative embodiment of another simple electrooptical device in accordance with the present invention. Components which are common between the embodiments of FIGS. 6 and 7 on the one hand and FIGS. 8 and 9 on the other hand are indicated in FIGS. 8 and 9 by primed numerals.

The electrooptical device of FIGS. 8 and 9 comprises an electrooptical component 10' including a core 18' in which a waveguide 20' is formed. Waveguide 20' has a higher index of refraction than the adjacent core portions 18'.

A cladding layer 22 lies adjacent to waveguide 20' (beneath waveguide 20 in the orientation of the embodiment illustrated in FIGS. 8 and 9). A separate, opposed cladding layer is not present in this embodiment, since the encapsulating layer 31 has a portion adjacent to (above in this embodiment) waveguide 20' and provides the cladding function. An electrode 25, which may be a negative electrode, and an electrode 27, which may be a positive electrode, are located in a plane parallel to the plane of the waveguide. In the embodiment of FIGS. 8 and 9, electrodes 25 and 27 are located in a layer above waveguide 20'. Electrodes 25 and 27 extend at least partially along the length of waveguide 20 parallel to the sides of the waveguide. Thus, each electrode of the pair is adjacent to an opposed side of the waveguide. Electric leads 36' and 38' are attached to electrodes 25 and 27, respectively, by solder or other suitable electrical connection means. An encapsulating or embedding layer 29 underlies cladding layer 22. As explained above, layer 31 combines both functions of cladding and encapsulation for waveguide 20 and electrodes 25 and 27, respectively.

Optical fibers 12' and 14' may be optically connected to component 10' in a manner similar to that described with respect to the embodiment of FIGS. 6 and 7. When the electrodes 25 and 27 are energized, an electric field vector extends from positive electrode 27 to negative electrode 25. The electric field vector extends through waveguide 20' in a direction transverse to the direction of the electric field of the embodiment illustrated in FIGS. 6 and 7.

Although only one waveguide is illustrated in only one core layer in the two embodiments of FIGS. 6 through 9, it would be readily apparent to one skilled in the art that a plurality of waveguides could be formed in a single layer or in multiple layers. If a plurality of waveguides are formed in the same core layer comprising an electrooptical composition containing the same electroactive compound of the present invention, then each waveguide of the plurality will have the same index of refraction. However, if the plurality of waveguides are formed in a plurality of different layers, where each layer contains a different electroactive compound of the present invention, then each waveguide system in each layer can independently carry signals and can be subject to interlayer transmission of signals by application of an appropriate electric field.

FIGS. 10a through 10d are used to illustrate a method of making the electroactive component comprising core 18 as used, for example, in electrooptical components illustrated in FIGS. 6 through 10. Core material 18 comprises an electroactive composition made electroactive by virtue of the alignment as described above of molecules of electroactive compounds of the present invention. The core material is illustrated as having a thickness "t" which, typically, is on the order of 1 to 100 microns, and, preferably, about 3 to 30 microns. These dimensions are consistent with the diameter or, in some instances, cross-sectional square dimension of optical fiber cores to which the waveguides are optically connected.

Figure 10A:
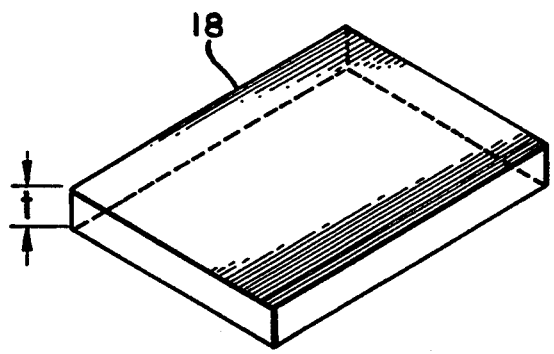
FIGS. 10a, 10b, 10c and 10d are a schematic representation in four views (a) through (d) to illustrate the production of an optical waveguide in a film made of a composition according to the present invention containing a novel electroactive compound.
Figure 10B:
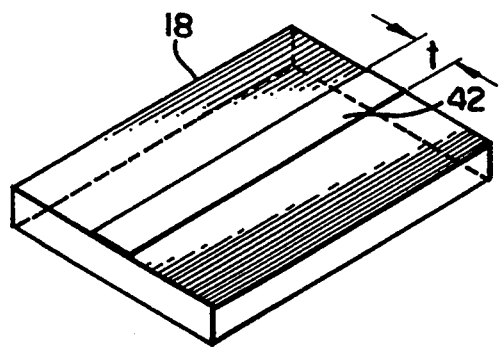

FIG. 10b illustrates the first step in the fabrication of a waveguide in an electrooptical film or core layer 18 after the preparation of the film itself. A mask 42 capable of masking light of a wavelength suitable to change the index of refraction of a material containing the electroactive compound overlies the portion of the film in which the waveguide is desired to be formed. Although mask 42 is illustrated as a straight rectangular mask having a width "t", it may be of any shape and have any width desired.

Figure 10C:
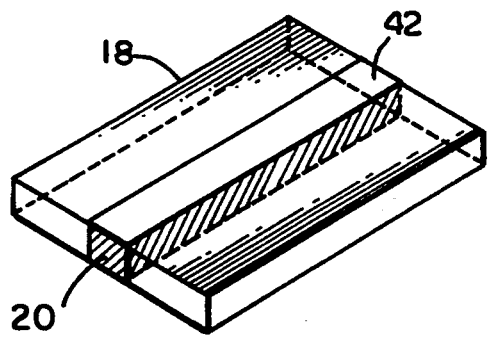
Figure 10D:
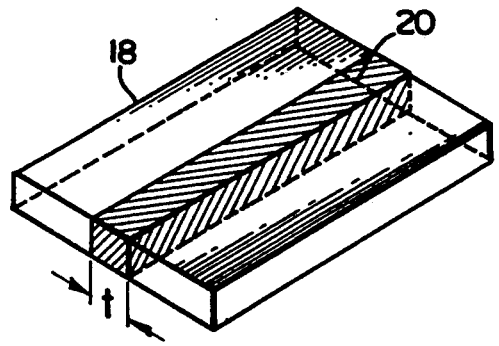

FIG. 10c illustrates the next step involved, that of irradiating the component 18 by light having a selected wavelength capable of changing the index of refraction in all areas of the component which are not protected by mask 42. Typically, long wavelength ultraviolet to visible absorption bands in the range of about 350 to about 700 nm are capable of inducing by absorption within these bands photobleaching of the electroactive compounds of the present invention by which their refraction undergoes a permanent change. Typically, the changes lower the index of refraction of any material containing the compounds. The photobleaching range of the bands of light or other optical radiation capable of causing a permanent change in refraction is a range in which most commercial compositions, films and coatings possess little or no optical absorption. Thus, it is possible to irradiate through transparent layers of the cover films and to photobleach a deeply embedded layer containing the electroactive compounds of the present invention to produce one or any number of waveguides, depending on the masking involved. If desired, the mask may remain on component 18 after it is irradiated with the photobleaching wavelength of light. However, the mask may also be removed by etching or other well-known techniques in the photolithographic art. What remains is a waveguide 20 as illustrated in FIG. 10d. Waveguide 20 has a width "t" corresponding to the same width of mask 42.

As explained above, it will be apparent to one skilled in the art that various types of electrooptical components and devices may be made using films or other compositions in which one or more waveguides have been formed according to the present invention. The schematic or diagrammatic embodiments illustrated in FIGS. 6 through 10d are merely for purposes of illustration and not intended to limit the scope of this application.

The electrooptical components and devices made using them according to the present invention are capable of modulating light by changing the electric field across the waveguides. Various electrooptical devices, including electrooptical modulators of the Mach-Zehnder type, the Franz-Keldysh type, multi-channel type and other types can be constructed using the present invention. In addition, passive integrated electrooptical circuits can be fabricated by standard photolithographic techniques by irradiating a multi-film sheet in which one layer contains an electroactive compound according to the present invention within the composition capable of undergoing an irreversible change in refraction upon radiation of a specific wavelength of light during the photolithographic process. Such a passive integrated circuit may be fabricated with two or more layers having different optical circuits independently introduced by selective lithography by employing different electroactive compounds according to the present invention which undergo irreversible changes in refraction with different wavelengths of light. An electroactive device can be produced using the multilayer passive integrated circuit containing two or more layers having the different optical circuits made as described above. Such an electroactive or electrooptical device permits switching of optical signals between successive layers.

The invention will now be described in more detail with reference to the following specific, non-limiting examples. Examples I through 20 are specific, illustrative working examples which have actually been performed. Examples 21 and 22 are proposed syntheses which are believed to be readily workable, although the specific syntheses of these two examples have not been performed.

Example 23 comprises a series of other specific working examples using various compounds based on the general procedure and general reaction equation set forth in the example.

EXAMPLE 1

Synthesis of 2-(4-Formylphenyl)-1,3-indandione

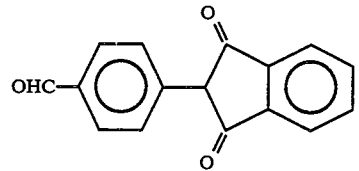

A solution of 476.6 parts terephthaldehyde mono(diethylacetal) and 268.2 parts phthalide in 391 parts ethyl propionate solvent was distilled in an atmosphere of argon gas until 222.8 parts of solvent are collected. To the distillation residue which consists of a homogeneous slightly yellow solution was added a solution of 408 parts sodium ethoxide in 1177 parts absolute ethanol over 30 minutes time in order to control the exothermic reaction. The resulting mixture, which now consists of a red suspension, was refluxed for 2 hours. After this reflux, 1177 parts of solvent was removed by distillation and 3147 parts glacial acetic acid and 720 parts 12 normal hydrochloric acid was added. The resulting mixture, which now consists of an orange suspension, was heated at 50' C. for 16 hours. After this time the mixture was heated to 70° C. and filtered hot. The solid on the filter was washed with 1049 parts boiling glacial acetic acid. The combined filtrate and wash, which contained the desired product, were diluted with 1000 parts water and filtered to give 500 parts of a red precipitate (quantitative yield). The precipitate was recrystallized from 85% methanol in water to give a 78% recovery of purified product, 2-(4-formylphenyl)-1,3-indandione as a maroon to red microcrystalline solid.

EXAMPLE 2

Synthesis of Sodium 4-Stilbazole-4'-dicyanomethylide

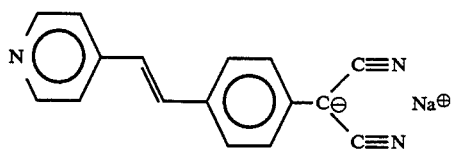

To 54.9 parts of a mineral oil dispersion containing 60% by weight sodium hydride was added a solution of 90.2 parts malononitrile dissolved in 100 parts tetrahydrofuran solvent. The resulting mixture was heated to 65' C. as a solution of 168.9 parts 4'-iodo-4-stilbazole and 19.2g bis(triphenylphosphine)palladium [II] chloride in 2000 parts tetrahydrofuran solvent was added. The resulting suspension was stirred and kept at 65' C. for seven days in an atmosphere of dry nitrogen while adequate tetrahydrofuran was added to maintain the reaction volume at 2.5L. The mixture was then cooled to ambient temperature and 1416 parts ethyl ether was added with stirring. The resulting suspension of yellow crystals was filtered. The yield of yellow microcrystalline sodium 4-stilbazole-4'-dicyanomethylide was 161.9 parts or 110% of the theoretically possible amount.

EXAMPLE 3

Synthesis of 4-Methyl-4-stilbazolium-4'-[2-(1,3-indandione-2-ide).]

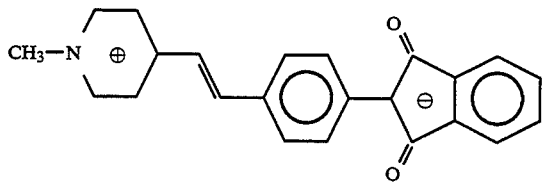

A mixture of 2.35 parts 1,4-dimethylpyridinium iodide and 2.38 parts 2-(4-formylphenyl)-1,3-indandione in 31.4 parts 2-propanol was heated to reflux as 3.9 parts of a 0.1 molar solution of piperidine acetate was added with no noticeable change. On addition of 0.86 part piperidine heat was evolved and a rapid color change from orange to black occurred. After reflux of this mixture for 16 hours, the hot mixture was filtered to yield 3.1 parts, or 91% of the theoretically possible amount, of black microcrystalline 4-methyl-4-stilbazolium--4'-[2-(1,3-indandione-2-ide)].

EXAMPLE 4

Synthesis of 4-(n-octadecyl)-4-stilbazolium-4'-[2-(1,3-indandione-2-ide)]

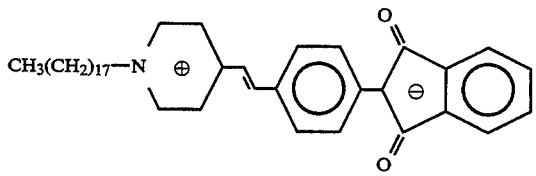

A mixture of 4,735 parts of 1-[1-(n-octadecyl)]-4-methylpyridinium iodide and 2.38 parts 2-(4-formylphenyl)-1,3-indandione in 31.4 parts 2-propanol was heated to reflux as 3.9 parts of a 0.1 molar solution of piperidine acetate in 2-propanol was added with no noticeable change. On addition of 0.86 part piperidine heat was evolved and a rapid color change from orange to brown occurred. After reflux of this mixture for 16 hours, the hot mixture was filtered to yield 5.3 parts, or 93.7% of the theoretically possible amount, of dull brown microcrystalline 4-(n-octadecyl)-4-stilbazolium-4'-[2-(1,3-indandione-2-ide)].

EXAMPLE 5

Synthesis of 4-Methyl-2,3-benzo-4-stilbazolium-4,-[2-(1,3-indandione-2-ide)]

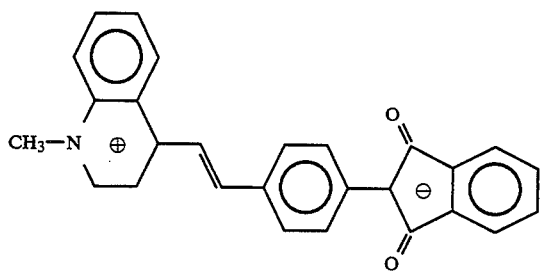

A mixture of 2.85 parts 1,4-dimethylquinolinium iodide and 2.38 parts 2-(4-formylphenyl)-1,3-indandione in 31.4 parts 2-propanol was heated to reflux as 3.9 parts of a 0.1 molar solution of piperidine acetate in 2-propanol was added with no noticeable change. On addition of 0.86 part piperidine heat was evolved and a rapid color change from orange to greenish black occurred. After reflux of this mixture for 16 hours, the hot mixture was filtered to yield 4.1 parts, or 100% of the theoretically possible amount, of greenish black microcrystalline 4-methyl-2,3-benzo-4,-stilbazolium-4'-[2-(1,3-indandione-2-]. [2-(1,3-indandione-2-ide)]

EXAMPLE 6

Synthesis of 4- (n-Octadecyl)-2,3-benzo-4-stilbazolium 4'-[2-(1,3-indandione-2-ide)]

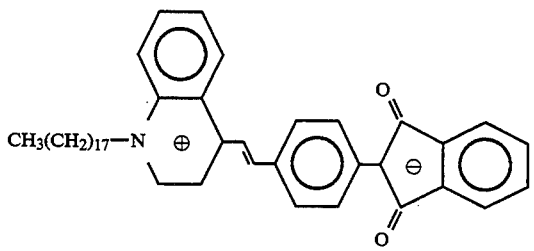

A mixture of 5,236 parts of 1-[1-(n-octadecyl)]-4-methylquinolinium iodide and 2.38 parts 2-(4-formylphenyl)-1,3-indandione in 31.4 parts 2-propanol was heated to reflux as 3.9 parts of a 0.1 molar solution of piperidine acetate in 2-propanol was added with no noticeable change. On addition of 0.86 part piperidine heat was evolved and a rapid color change from orange to blue occurred. After reflux of this mixture for 16 hours, the hot mixture was filtered to yield 5.4 parts, or 87.7% of the theoretically possible amount, of very dark dull blue microcrystalline 4-(n-octadecyl)-2,3-benzo-4-stilbazolium -4'-[2-(1,3-indandione-2-ide)].

EXAMPLE 7

Synthesis of 4-Methyl-4-stilbazolium-4'-dicyanomethylide

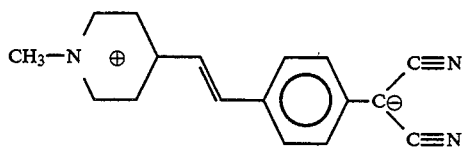

To a refluxing mixture of 13.5 parts sodium 4-stilbazole-4'-dicyanomethylide and 32,720 parts acetone is added 8.9 parts dimethyl sulfate and the whole is refluxed with continuous stirred in an argon atmosphere. The resulting mixture was a suspension of shiny purple crystals. The shiny purple crystals, which were removed by filtration, consisted of 9 parts of 4-methyl-4-stilbazolium-4'-dicyanomethylide or 69% of the theoretically possible amount.

EXAMPLE 8

Synthesis of 4-(n-Octadecyl)-4-stilbazolium-4'-dicyanomethylide

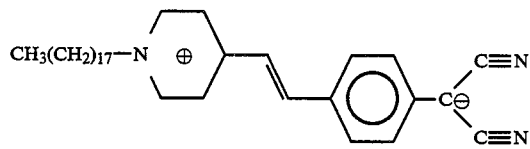

To 654.4 parts boiling acetone was added 27 parts sodium 4-stilbazole-4'-dicyanomethylide, 37 parts tetrabutylammonium iodide, and 57 parts 1-iodooctadecane and the whole was stirred under continuous reflux in an atmosphere of dry argon for 66 hours. On cooling to ambient temperature, 800 parts of water was added which caused a thick oily semisolid to precipitate. This semisolid was separated by decantation and washed with 1000 parts of a solution of 100 parts acetone in 900 parts ether and, finally, with 1000 parts hexane. The solid which remained was recrystallized from 180 parts ethyl acetate to yield 4.5 parts of very dark blue microcrystalline 4-(n-octadecyl)-4-stilbazolium-4'-dicyanomethylide or 9% of the theoretically possible amount.

EXAMPLE 9

Synthesis of 4-(2,2,3,3,4,4,5,5,6,6,7,7,8,8,8-pentadecafluoro-n-octyl)-4-stilbazolium-4'-dicyanomethylide

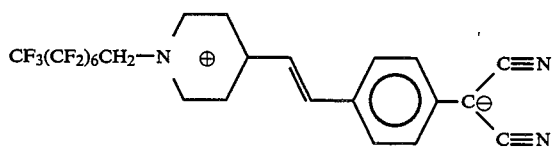

To a solution of 2.7 parts sodium 4-stilbazole-4'-dicyanomethylide in 20.7 parts 1-methyl-2-pyrrolidinone is added 5.3 parts 2,2,3,3,4,4,5,5,6,6,7,7,8,8,8-pentadecafluoro-n-octyl trifluoromethanesulfonate and the whole was stirred for 18 hours while the temperature was maintained at 50° C. by the external application of heat. After this time an additional 5.3 parts of 2,2,3,3,4,4,5,5,6,6,7,7,8,8,8-pentadecafluoro-n-octyl trifluoromethanesulfonate was added and the whole was maintained at 50° C. by external application of heat for 18 hours. The resulting mixture was cooled to ambient temperature and filtered to yield 1.0 parts of shiny aqua crystals of 4-(2,2,3,3,4,4,5,5-6,6,7,7,8,8,8-pentadecafluoro-n-octyl)-4-stilbazolium4'-dicyanomethylide or 16% of the theoretically possible amount.

EXAMPLE 10

Synthesis of 4,4'-Bis-(N,N-diethylamino)-4''-fluorotriphenylmethyl perchlorate

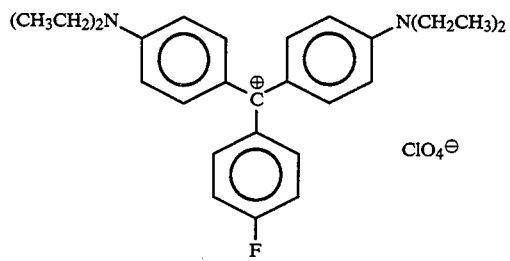

To a solution of 279 parts 4-fluorophenylmagnesium bromide dissolved in 992 parts tetrahydrofuran solvent was added 400 parts 4,4'-bis-(N,N-diethylamino)-benzophenone dissolved in 620 parts tetrahydrofuran solvent. After standing without external application of heat for 1 hour, the temperature of the resulting solution rose to 40° C. The solution was then refluxed by the application of external heat for 4 hours and then allowed to stand for 16 hours at ambient temperature. With rapid mechanical stirring 30 parts water and 210 parts glacial acetic is added resulting in a thick dark green paste. This paste was heated to reflux. With provision for the removal of volatile solvent by distillation, 3000 parts boiling water was added to the stirred and boiling paste. During this process 886 parts of volatile solvent distilled which was discarded. The resulting reaction mass consisted of a very dark green solution. This solution was cooled to ambient temperature as, with rapid stirring, 200 parts anhydrous sodium perchlorate dissolved in 300 parts water was added. The resulting mixture consisted of a thick, very dark green paste covered by a clear liquid layer. The upper liquid layer was removed by decantation and discarded. The lower layer of green paste was stirred with 3000 parts water and allowed to settle. The resulting mixture consisted of a thick, very dark green paste covered by a clear liquid layer. The upper liquid layer was removed by decantation and discarded. The lower layer of green paste was dissolved in 2454 parts acetone to form a dark green solution. To this dark green solution is added with rapid stirring 2124 parts ethyl ether which precipitated a dark green crystalline material. The crystalline material is removed by filtration and dried at 50° C. in vacuo to yield 513 parts of dark green microcrystalline 4,4'-bis-(N,N-diethylamino)-4''-fluorotriphenylmethyl perchlorate or 83% of the theoretically possible amount.

EXAMPLE 11

Synthesis of 4,4'-Bis-(N,N-dimethylamino)-4''-fluorotriphenylmethyl perchlorate

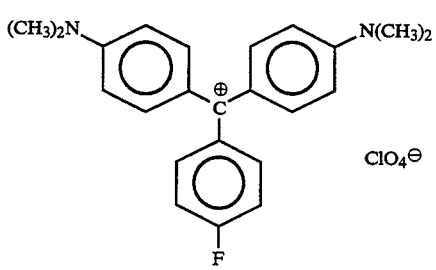

The procedure applied for 4'-bis(N,N-diethylamino)-4''-fluorotriphenylmethyl perchlorate as in Example 10 was applied exactly except that 228 parts 4,4'-bis-(N,N-dimethylamino)-benzophenone was used instead of 4,4'-bis-(N,N-diethylamino)-benzophenone. The yield of dark green microcrystalline 4,4'-bis-(N,N-dimethylamino)-4''-fluorotriphenylmethyl perchlorate was 242 parts or 54% of the theoretically possible amount.

EXAMPLE 22

Synthesis of 4,4'-Bis-[N,N-di-(n-butyl)amino]-4''-fluorotriphenylmethyl perchlorate

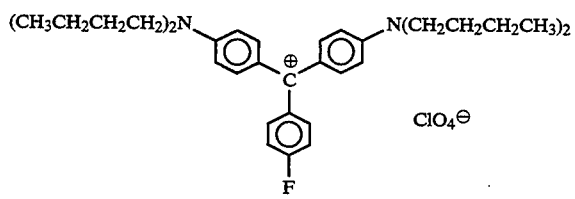

To a solution of 48.4 parts 4-fluorobenzaldehyde and 320 parts N,N-di-(n-butyl)-aniline is added, with rapid stirring, a solution of 28.2 parts hydrogen chloride in 62.8 parts water. The resulting mixture is mechanically stirred while being maintained at a temperature of 125° C. for 66 hours. On cooling to ambient temperature and settling the mixture consisted of a thick oily lower layer and a more mobile, clear upper layer. The upper layer was removed by decantation and discarded. The lower oily layer was dissolved in 1049 parts glacial acetic acid and this solution was stirred for 18 hours after the addition of 175.6 parts of lead tetraacetate. To the resulting solution was added a solution of 43.1 parts perchloric acid, 64.7 parts water and 525 parts glacial acetic acid. The resulting mixture consisted of dark green crystals suspended in a dark green clear liquid. To this mixture was then added 400 parts water over 2 hours with rapid stirring. The crystalline material was removed by filtration and dried at 70° C. in vacuo to yield 144.4 parts of dark green shiny microcrystalline 4,4'-bis-[N,N-di-(n-butyl)amino]-4''-fluorotriphenylmethyl perchlorate or 59% of the theoretically possible amount.

EXAMPLE 13

Synthesis of 4-(N,N-dimethylamino)-4'-fluoro-2'',4'',-6''-trimethyltriphenylmethyl perchlorate

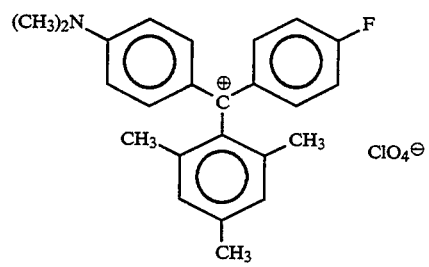

To a solution of 2.4 parts 4-(N,N-dimethylamino)-4'-fluorobenzophenone dissolved in 21.3 parts tetrahydrofuran solvent was added 4.5 parts 2,4,6-trimethylphenylmagnesium bromide dissolved in 13.3 parts tetrahydrofuran solvent and the resulting solution was allowed to stand at ambient temperature for eighteen hours. To this solution was added with rapid stirring a solution containing 3.0 parts perchloric acid, 1.3 parts water, and 10.5 parts glacial acetic acid which results in the precipitation of dark red crystals. The crystalline material is removed by filtration to yield 3.5 parts of red microcrystalline 4-(N,N-dimethylamino)-4'-fluoro-2'',4'',6''-trimethyltriphenylmethyl perchlorate or 80% of the theoretically possible amount.

EXAMPLE 14

Synthesis of 3-[4,4'-Bis-(N,N-diethylamino)-benzhydrylidene]-6-(1,3-indandione-2-ylidene)-1,4-cyclohexadiene

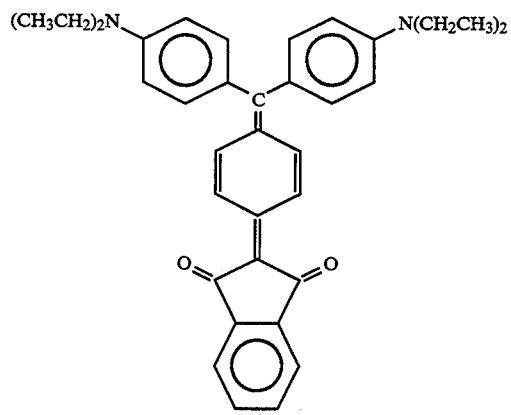

To a solution of 37 parts potassium t-butoxide and 48 parts 1,3-indandione in 1030 parts 1-methyl-2-pyrrolidinone is added 146 parts 4,4'-bis-(N,N-diethylamino)-4''-fluorotriphenylmethyl perchlorate. The resulting solution is heated to 130° C. for 4 hours and cooled to ambient temperature whereupon a solution of 31.8 parts sodium carbonate in 468 parts water was added. The dark blue-violet crystalline solids which precipitated are removed by filtration and washed on the filter consecutively with 10,000 parts boiling water; 1000 parts of a solution of 500 parts methanol and 500 parts water; and 710 parts ethyl ether. The yield of dark blue-violet microcrystalline 3-[4,4'-bis-(N,N-diethylamino)-benzhydrylidene]        -6-(1,3-indandione-2-ylidene)-1,4- cyclohexadiene is 74 parts or 40% of the theoretically possible amount.

EXAMPLE 15

Synthesis of 3-[4,4'-Bis-(N,N-dimethylamino)-benzhydrylidene]-6-(1,3-indandione -2-ylidene)-1,4-cyclohexadiene

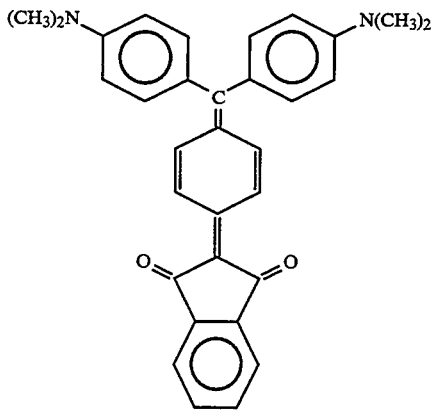

To a solution of 37 parts potassium t-butoxide and 48 parts 1,3-indandione in 1030 parts 1-methyl-2-pyrrolidinone was added 129 parts 4,4'-bis-(N,N-dimethylamino)-4"-fluorotriphenylmethyl perchlorate. The resulting solution is heated to 130° C. for 4 hours and cooled to ambient temperature whereupon a solution of 31.8 parts sodium carbonate in 468 parts water was added. The black crystalline solids which precipitated are removed by filtration and washed on the filter consecutively with 10,000 parts boiling water; 1000 pans of a solution of 500 parts methanol and 500 parts water; and 710 parts ethyl ether. The yield of black microcrystalline 3-[4,4' -bis-(N,N-dimethylamino)-benzhydrylidene]-6-(1,3-indandione-2ylidene)-1,4-cyclohexadiene was 78 parts or 46% of the theoretically possible amount.

EXAMPLE 16

Synthesis of 7,7-Bis-[4-(N,N-dimethylamino)-phenyl]-8,8-dicyanoquinodimethane

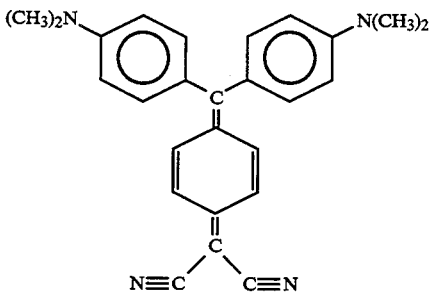

To a solution of 8 parts sodium hydride and 22 parts malononitrile in 103 parts 1-methyl-2-pyrrolidinone was added 129 parts 4,4'-bis-(N,N-dimethylamino)-4"-fluorotriphenylmethyl perchlorate. The resulting solution is heated to 140° C. for 5 hours and cooled to ambient temperature whereupon a solution of 31.8 parts sodium carbonate in 468 parts water is added. The dark violet crystalline solids which precipitated was removed by filtration and washed on the filter consecutively with 10,000 parts boiling water; 1000 parts of a solution of 500 parts methanol and 500 parts water; and 710 parts ethyl ether. The yield of dark violet microcrystalline 7,7-bis-[4-(N,N--dimethylamino)-phenyl]-8,8-dicyanoquinodimethane is 64 parts or 54% of the theoretically possible amount.

EXAMPLE 17

Synthesis of 7,7-Bis-[4-(N,N-diethylamino)-phenyl]-8,8-dicyanoquinodimethane

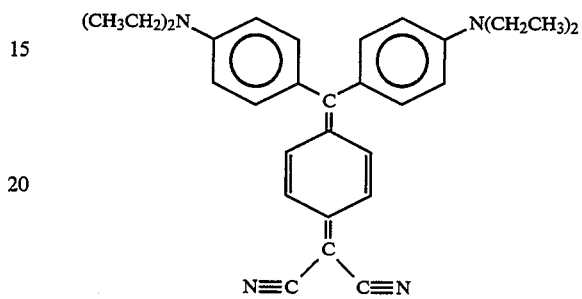

To a solution of 8 parts sodium hydride and 22 parts malononitrile in 103 parts 1-methyl-2-pyrrolidinone is added 146 parts 4,4'-bis-(N,N-diethylamino)-4"-fluorotriphenylmethyl perchlorate. The resulting solution is heated to 140° C. for 5 hours and cooled to ambient temperature whereupon a solution of 31.8 parts sodium carbonate in 468 parts water is added. The dark violet crystalline solids which precipitated was removed by filtration and washed on the filter consecutively with 10,000 parts boiling water; 1000 parts of a solution of 500 parts methanol and 500 parts water; and 710 parts ethyl ether. The yield of dark violet microcrystalline 7,7-bis-[4-(N,N-diethylamino)-phenyl]-8,8-dicyanoquinodimethane is 69 parts or 51% of the theoretically possible amount.

EXAMPLE 18

Synthesis of 7,7-Bis-(4-[di-(n-buty)amtno]-phenyl)8-dicyanoquinodimethane

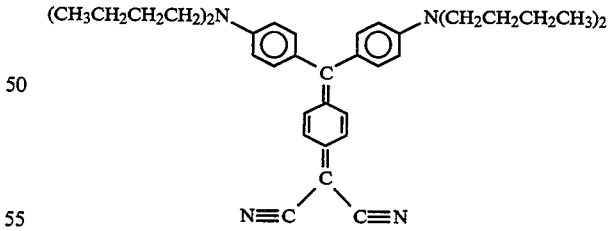

To a solution of 44.3 parts malononitrile in 1033 parts 1-methyl-2-pyrrolidinone solvent cooled to 15° C. by external application of an ice bath was added with rapid stirring 76.8 parts potassium t-butoxide. The resulting solution was heated to 40° and stirred as 200 parts 4,4'-bis-[di-(n-butyl)amino]-4"-fluorotriphenylmethyl perchlorate and 517 parts 1-methyl-2-pyrrolidinone is added. The resulting red solution was heated to 150° C. with continuous rapid stirring for 6 hours under argon. The resulting mixture was cooled to 80° C. and kept at that temperature while 1186.5 parts methanol was added with continued stirring. The resulting mixture was cooled to 65° C. and the source of heat was removed. To the resulting mixture 750 parts water was added over 66 hours with continued stirring resulting in a suspension of fine, shiny green crystals. These crystals were removed by filtration and washed with 1186.5 parts methanol. The resulting wet crystalline green solids were added to a boiling rapidly stirred mixture of 2185 parts benzene, 22 parts decolorizing carbon and 22 parts sodium sulfate. This mixture was filtered hot and the liltrate cooled to ambient temperature. This liltrate deposited brilliant green crystals which were removed by filtration and dried in vacuo to yield 125 parts of shiny green crystals of 7,7-bis-(4-[di-(n-butyl)amino]-phenyl)-8,8-dicyanoquinodimethane or 70% of the theoretical amount.

EXAMPLE 19

Synthesis of
7-[4-(N,N-Dimethylamino)-phenyl]-7-(2,4,6-trimethyl-phenyl)-8,8-dicyanoquinodimethane

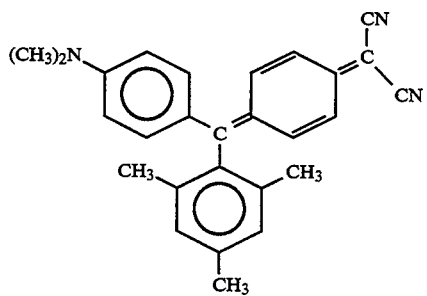

To a rapidly stirred mixture of 166.2 parts potassium t-butoxide and 393 parts acetonitrile maintained in the temperature range of 5° C. to 10° C. by external cooling was added a solution of 93.2 parts malononitrile dissolved in 78.6 parts acetonitrile solvent over one-half hour. To the resulting mixture with continued stirring a solution of 300 parts 4-(N,N-dimethylamino)-2',4',6'-trimethyl-4''-fluorotriphenylmethyl perchlorate in 707.4 parts acetonitrile was added. After stirring for 6 hours, the mixture was added to 2000 parts water and the dark red oil which separated was removed by decantation. This oil was dissolved in 1000 parts ethyl ether and chromotagraphed over a column of neutral alumina with separation of those fractions eluted with 2000 parts ethyl ether which were blue in color. Evaporation of these fractions yielded 75.4 parts of dark red to brown microcrystalline 7-[4-(N,N-dimethylamino)-phenyl]-7-(2,4,6-trimethylphenyl)-8,8-dicyanoquinodimethane or 29% of the theoretically possible amount.

EXAMPLE 20

Synthesis of Crosslinked Polystyrene with Pendant 4-Methylene-4-stilbazolium-4-[2-(1,3-indandione-2--ide)]Groups To 71.8 parts 4-methylpyridine preheated to 50° C. is added 10 parts 200 mesh chloromethylated crosslinked polystyrene beads containing 7 milliequivalents chlorine per gram and 1% divinylbenzene as the crosslinking agent. The resulting mixture was maintained at a temperature of 50° C. for eighteen hours during which time the color of the mixture changed from white to deep peach. The resulting suspension was filtered while hot and the beads on the filter were washed with 196.3 parts 2-propanol. The resulting beads were refluxed in 78.5 parts 2-propanol for eighteen hours. The beads were isolated by filtration and washed twice with 39.7 part portions of 2-propanol. The resulting beads were then added to a solution of 33.4 parts 2-(4-formyl-phenyl)-1,3-indandione; 10.6 parts piperidine; and 0.42 parts glacial acetic in 235.5 parts 2-propanol solvent and the resulting mixture heated at reflux for eighteen hours during which time the coloration of the beads changed from peach to black. The resulting mixture was filtered and the liltrate discarded. The black beads on the filter were slurtied three consecutive times with a solution consisting of 102.3 parts acetone and 98.1 parts 2-propanol. The yield of free flowing black beads of crosslinked polystyrene with pendant 4-methylene-4-stilbazolium-4'-[2-(1,3-indandione-2-ide]groups was 13.6 parts.

EXAMPLE 21

Proposed Synthesis of
4-(Dicyanomethyl)-benzaldehyde

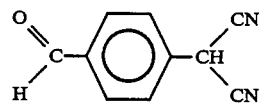

To a 0.10 formula weight of sodium hydride suspended in 1 L acetonitrile in an atmosphere of dry argon is added 0.11 mole malononitrile dissolved in 0.10 L acetonitrile while adequate external cooling is applied to maintain the temperature of the reaction mixture in the range 0° C. to 10° C. To this mixture 0.05 formula weight of 4-iodobenzaldehyde is added followed by a solution of 0,005 formula weight of tetrakis(triphenyl-phosphene)palladium[0] in 0.50L argon-saturated acetonitrile. The resulting mixture is refluxed under argon with rapid stirring for 66 hours. The resulting mixture is concentrated in vacuo to a volume of 100 ml and the resulting mixture is treated with 500 ml ethyl ether. The salt which precipitated is removed by filtration and, while not with ether, suspended in 0.5 L water. The resulting suspension is acidified to pH=1.0 with concentrated hydrochloric acid to precipitate the 4-(dicyanomethyl)benzaldehyde.

EXAMPLE 22

Proposed Synthesis of
4-(Dicyanomethyl)-benzaldehyde

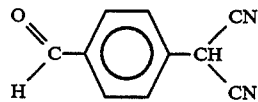

To a 0.10 formula weight of sodium hydride suspended in 1 L acetonitrile in an atmosphere of dry argon is added 0.11 mole malononitrile dissolved in 0.10 L acetonitrile while adequate external cooling is applied to maintain the temperature of the reaction mixture in the range 0° C. to 10° C. To this mixture 0.05 formula weight of 4'-iodo-2,2-dicyanostyrene is added followed by a solution of 0.005 formula weight of tetrakis(tri-phenylphosphene) palladium [0] in 0.50 L argon-saturated acetonitrile. The resulting mixture is refluxed under argon with rapid stirring for 66 hours. The resulting mixture is concentrated in vacuo to a volume of 100 ml and the resulting mixture is treated with 50 ml ethyl ether. The salt which precipitated is removed by filtration and, while not with ether, suspended in 0.5 L water. The resulting suspension is steam distilled in a current of dry argon and the steam distillate discarded. The residue in the distillation flasks is cooled under argon, diluted to 0.5 L with water, and acidified to pH 1.0 with concentrated hydrochloric acid to precipitate the 4-(dicyanomethyl)-benzaldehyde.

EXAMPLE 23

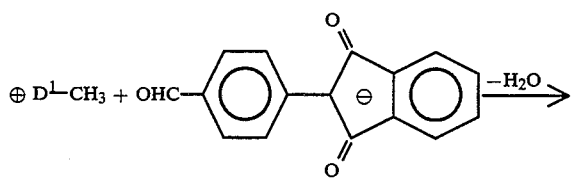

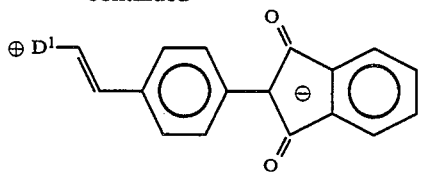

General Procedure

With reference to the following Table A, a solution of AA parts $+D^1\text{-}CH_3$ $I\ominus$; 100 parts 2-(4-formylphenyl)-1,3-indandione; 36 parts piperidine and 1.2 parts glacial acetic acid in 3,868 parts 2-propanol was stirred while heating under reflux for BB hours. On cooling to ambient temperature, the mixture was filtered and the filtrate discarded. The material on the filter was washed consecutively with 2,000 parts 2-propanol, 2,000 parts methanol and 2,500 parts ethyl ether. The resulting material was dried for 17 hours at 55° C. in vacuo. The yield of CC parts of product was DD% of the theoretically possible amount. The product was colored EE in the pure state, and the coloration of a saturated solution in dimethyl sulfoxide was FF and a saturated solution in tetrahydrofuran was colored GG.

TABLE A

| ⊕D1-CH3 | AA Parts | BB Hours | CC Parts | DD % Yield | EE Color | FF Color | GG Color | "PRODUCT" |
|---|---|---|---|---|---|---|---|---|
| (methyl-methylthiazolidinylidene cation) | 122 | 19 | 110 | 79 | black | violet | greenish-blue | (indanedione-phenyl-vinyl-methylthiazolidinylidene product) |
| (octadecyl-methylthiazolidinylidene cation) | 241 | 19 | 170 | 73 | black | violet | blue | (indanedione-phenyl-vinyl-octadecylthiazolidinylidene product) |
| (methyl-methylbenzoselenazolium cation) | 169 | 19 | 160 | 90 | brownish-black | blue | green | (indanedione-phenyl-vinyl-methylbenzoselenazole product) |
| (methyl-diphenyl-oxazolium cation) | 139 | 21 | 100 | 78 | black | violet | blue | (indanedione-phenyl-vinyl-diphenyl-methyloxazole product) |

TABLE A-continued
| ⊕D¹—CH₃ | AA Parts | BB Hours | CC Parts | DD % Yield | EE Color | FF Color | GG Color | "PRODUCT" |
|---|---|---|---|---|---|---|---|---|
| 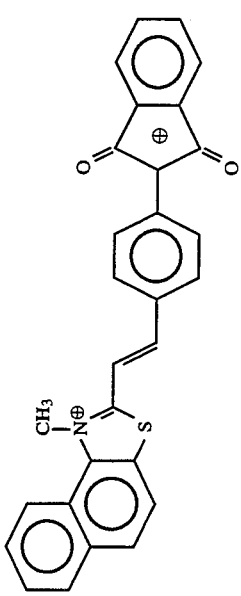 | 170 | 21 | 175 | 98 | black | green | yellowish-green | 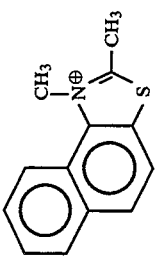 |

TABLE 1
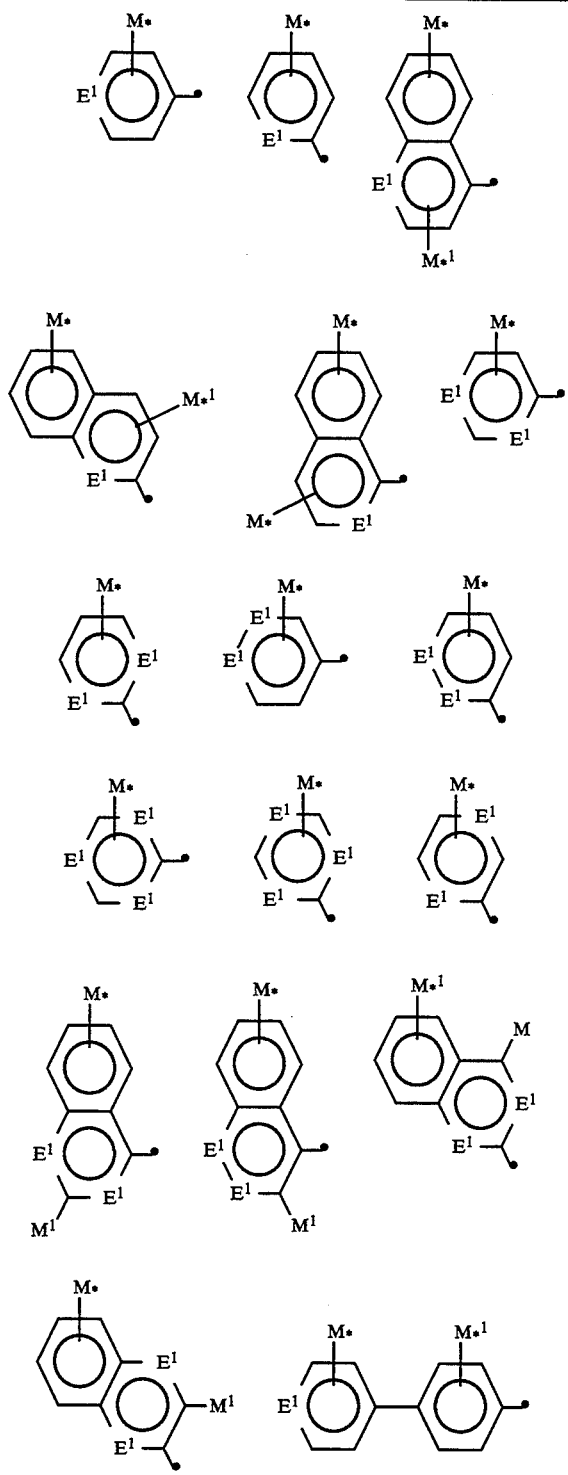
TABLE 1-continued
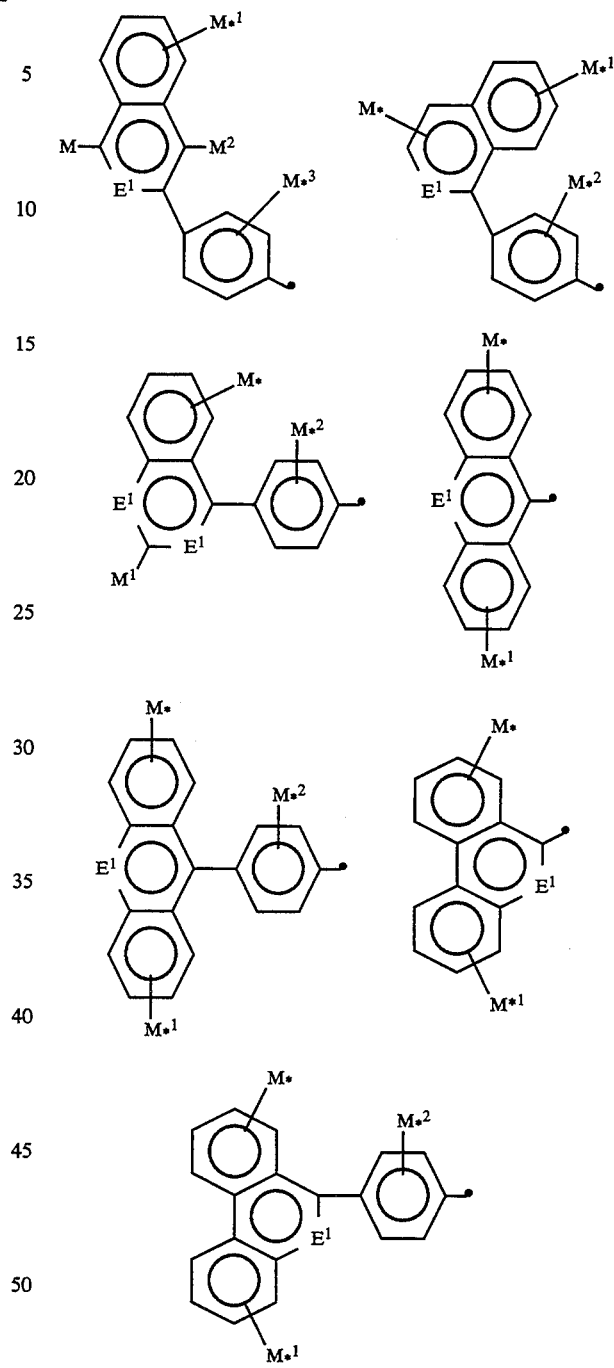
Each $E^1$ = N, P, As or Sb.
Any of M, $M^1$, $M^2$ or $M^3$ is independently any one of J, L, $R^1$, $R^2$, G—$R^3$ or Q.
The subscript "*" signifies the number of available valences for the substituents.
TABLE 2
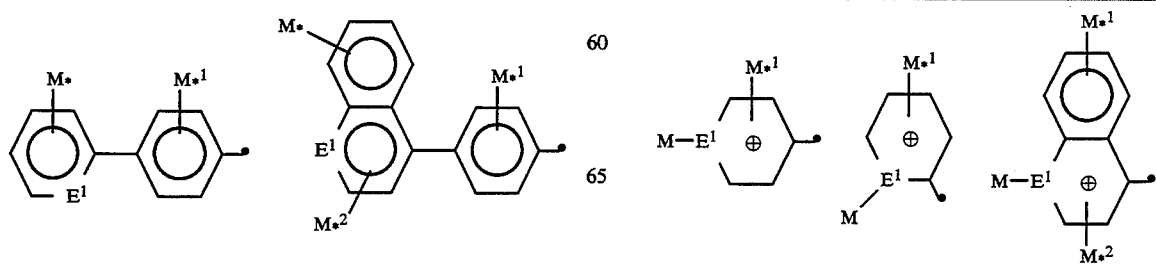

TABLE 2-continued
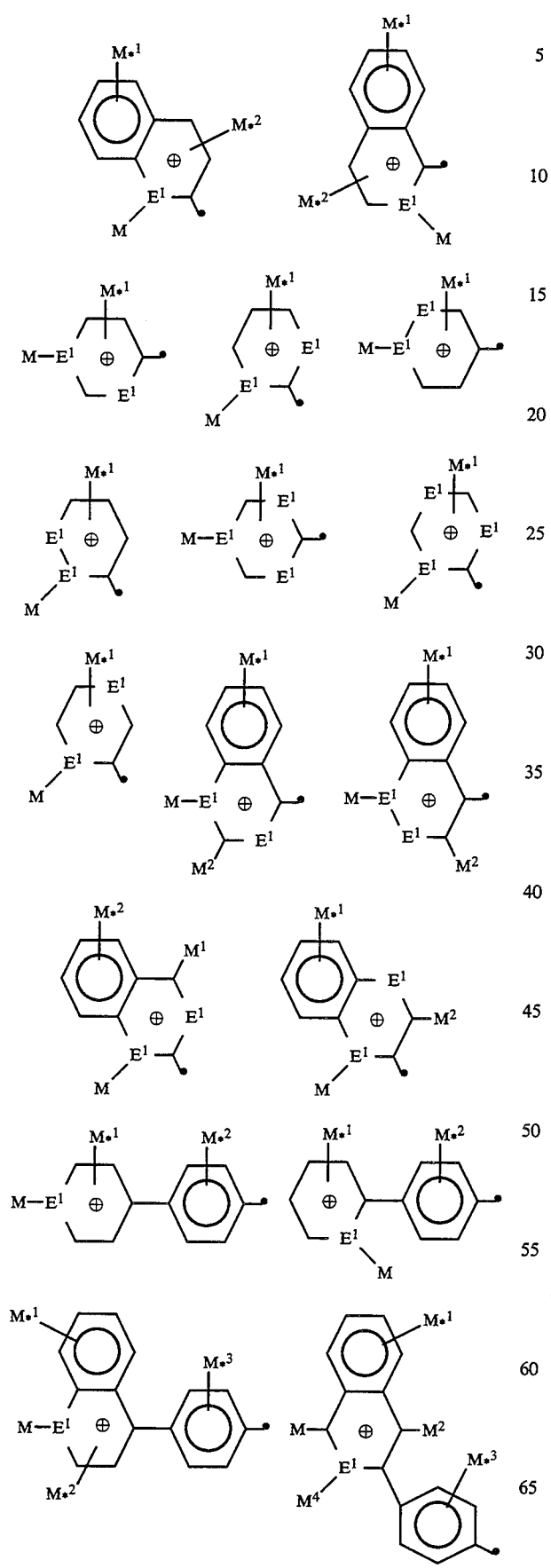
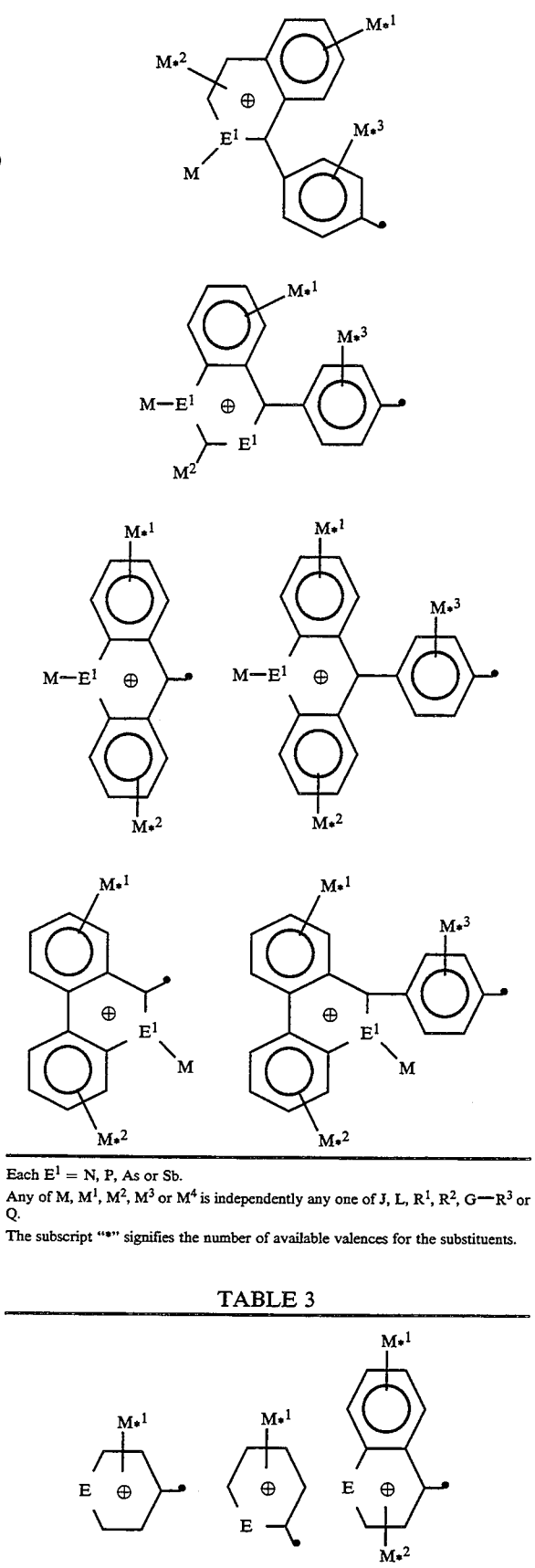
Each $E^1$ = N, P, As or Sb.
Any of M, $M^1$, $M^2$, $M^3$ or $M^4$ is independently any one of J, L, $R^1$, $R^2$, G—$R^3$ or Q.
The subscript "*" signifies the number of available valences for the substituents.
TABLE 3

TABLE 3-continued
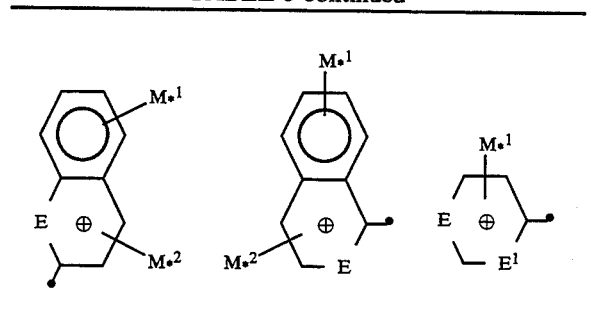
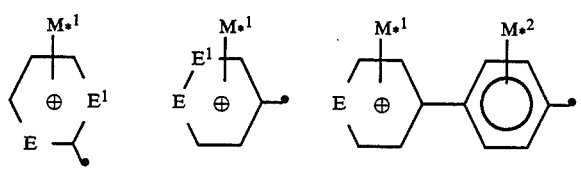
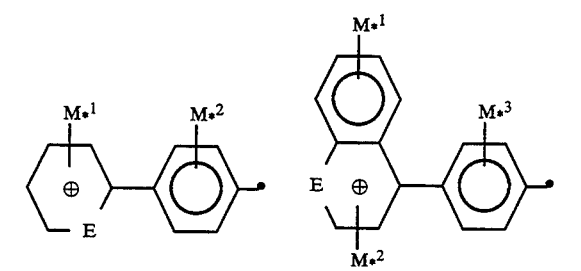
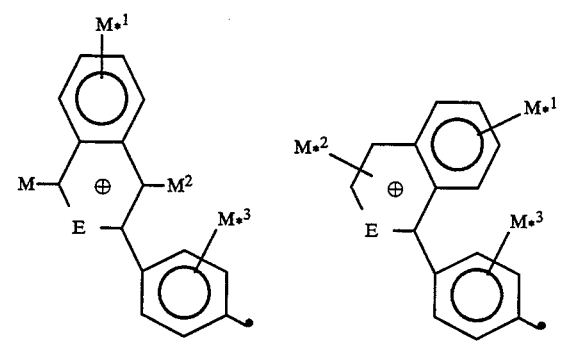
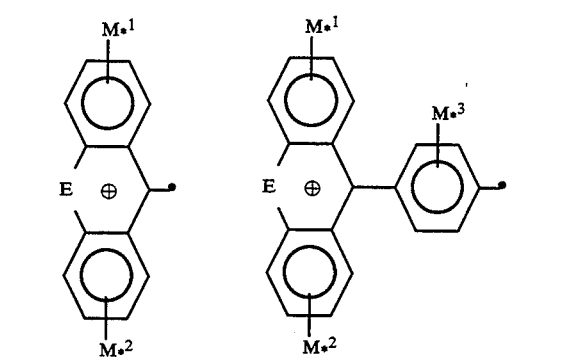
TABLE 3-continued
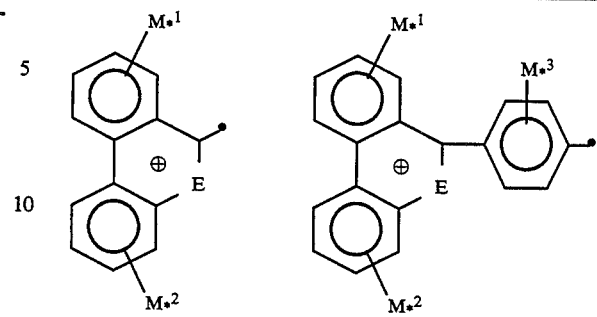
Each E = O, S, Se or Te.
Each $E^1$ = N, P, As or Sb.
Any of M, $M^1$, $M^2$ or $M^3$ is independently any one of J, L, $R^1$, $R^2$, G—$R^3$ or Q.
The subscript "*" signifies the number of available valences for the substituents.
TABLE 4
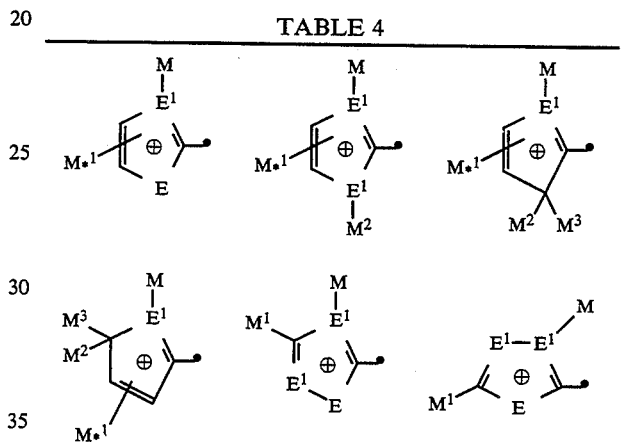
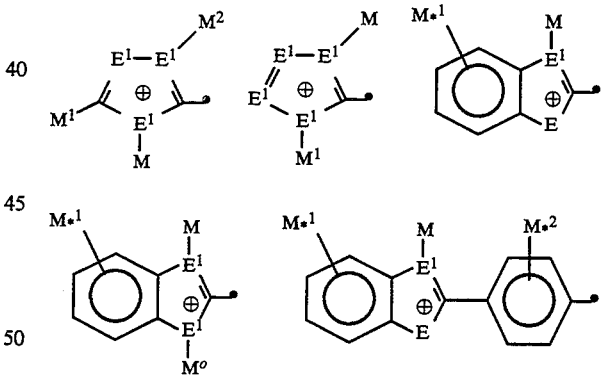
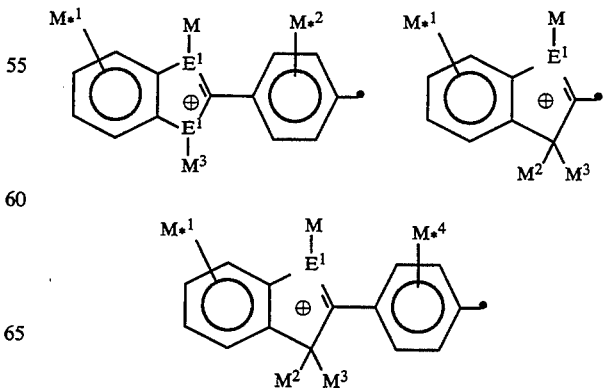

TABLE 4-continued

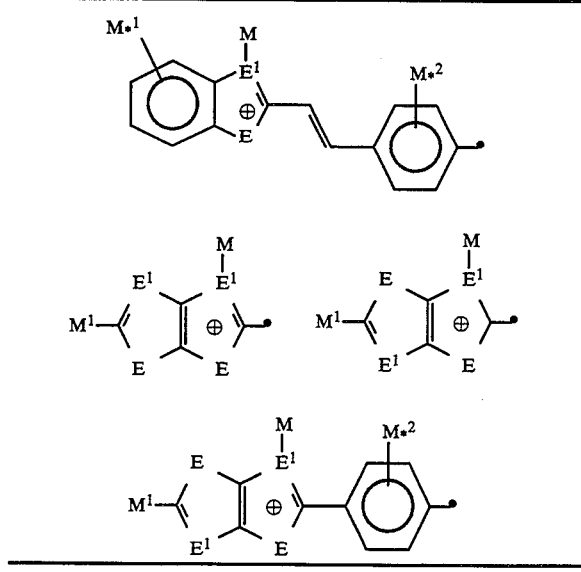

Each E = O, S, Se or Te.
Each $E^1$ = N, P, As or Sb.
Any of M, $M^1$, $M^2$, $M^3$ or $M^4$ is independently any one of J, L, $R^1$, $R^2$, G—$R^3$ or Q.
The subscript "*" signifies the number of available valences for the substituents.

TABLE 5

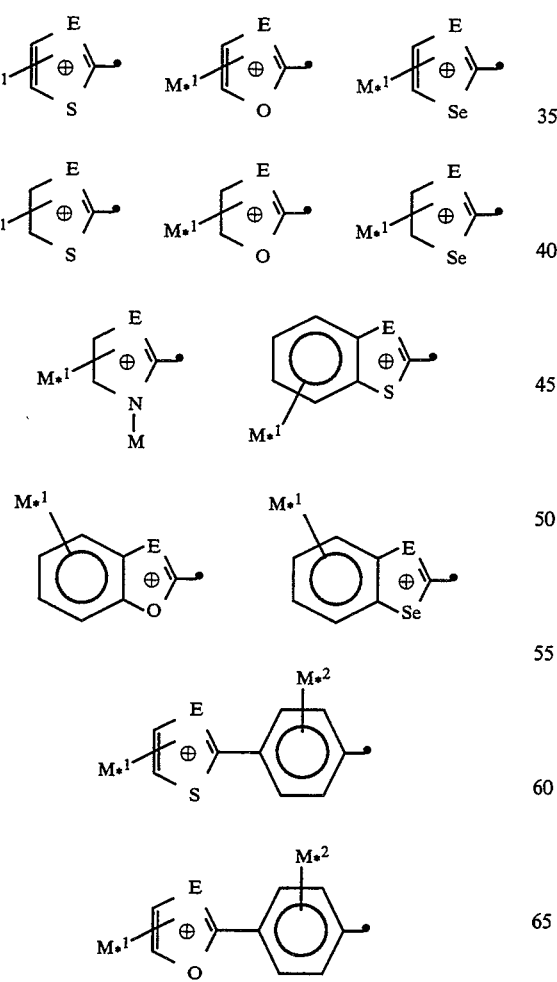

TABLE 5-continued

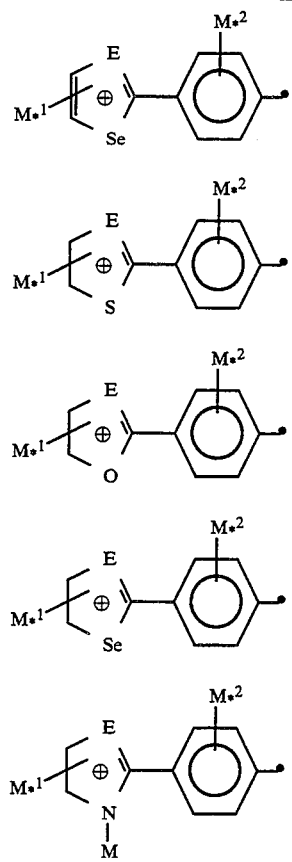

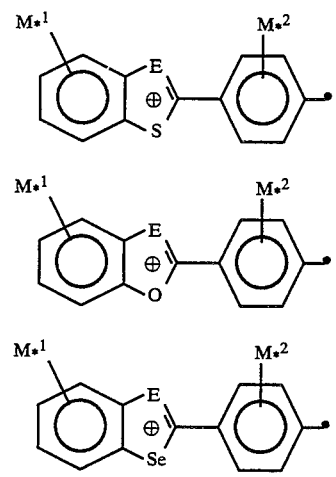

Each E = O, S, Se or Te.
Any of M, $M^1$, $M^2$ or $M^3$ is independently any one of J, L, $R^1$, $R^2$, G—$R^3$ or Q.
The subscript "*" signifies the number of available valences for the substituents.

TABLE 6

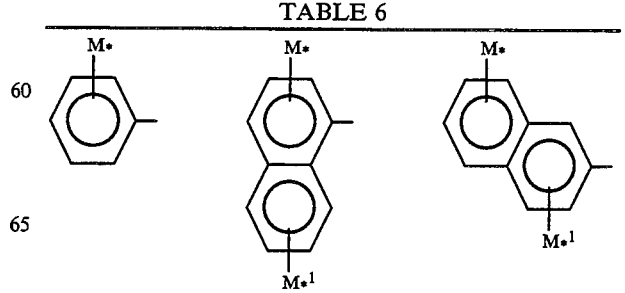

TABLE 6-continued
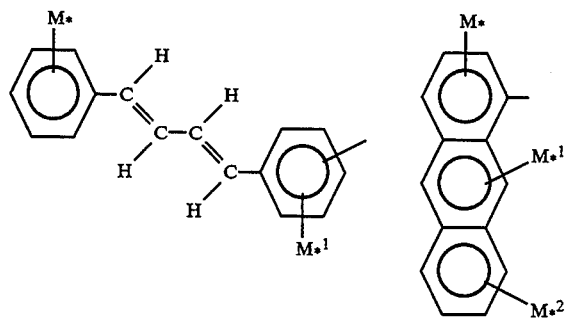
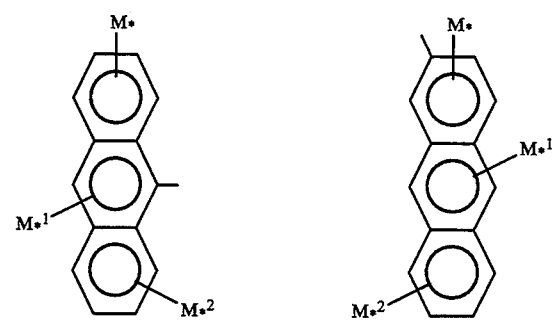
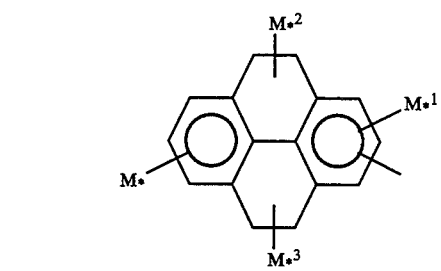
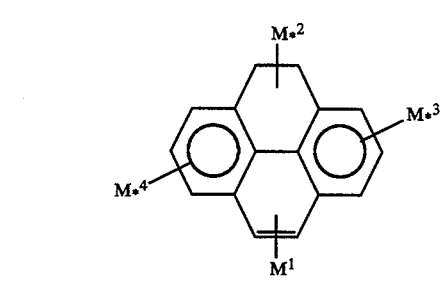
TABLE 6-continued
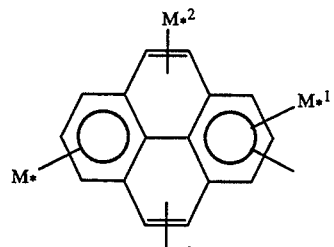
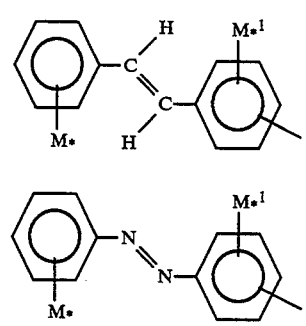
Any of M, M¹, M² or M³ is independently any one of J, L, R¹, R², G—R³ or Q. The subscript "*" signifies the number of available valences for the substituents.
TABLE 7
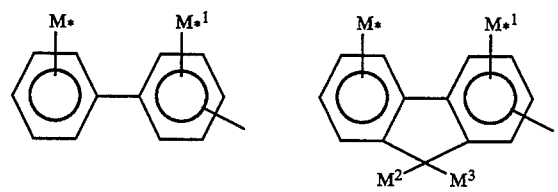
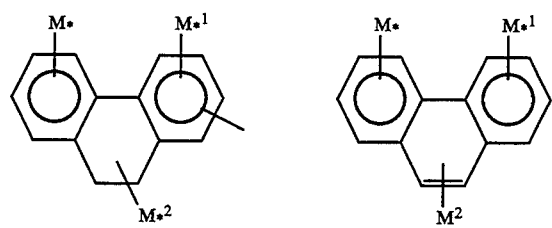
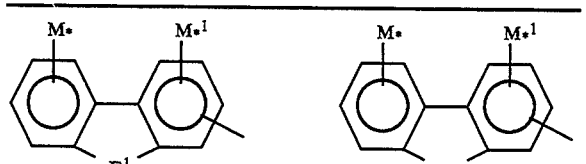
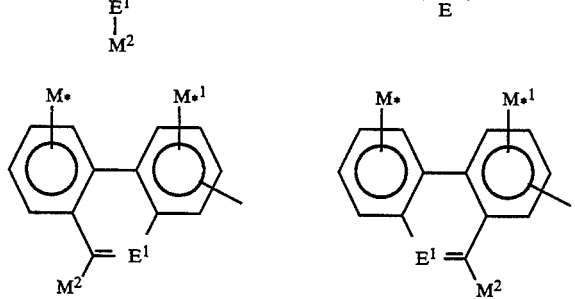
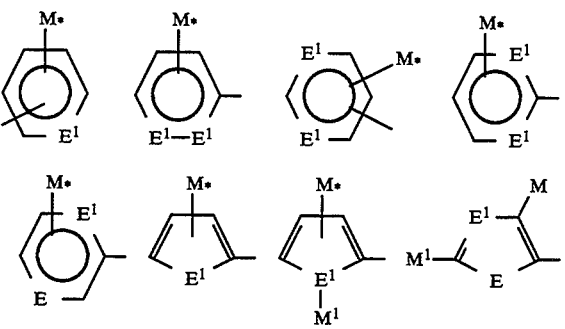

TABLE 7-continued
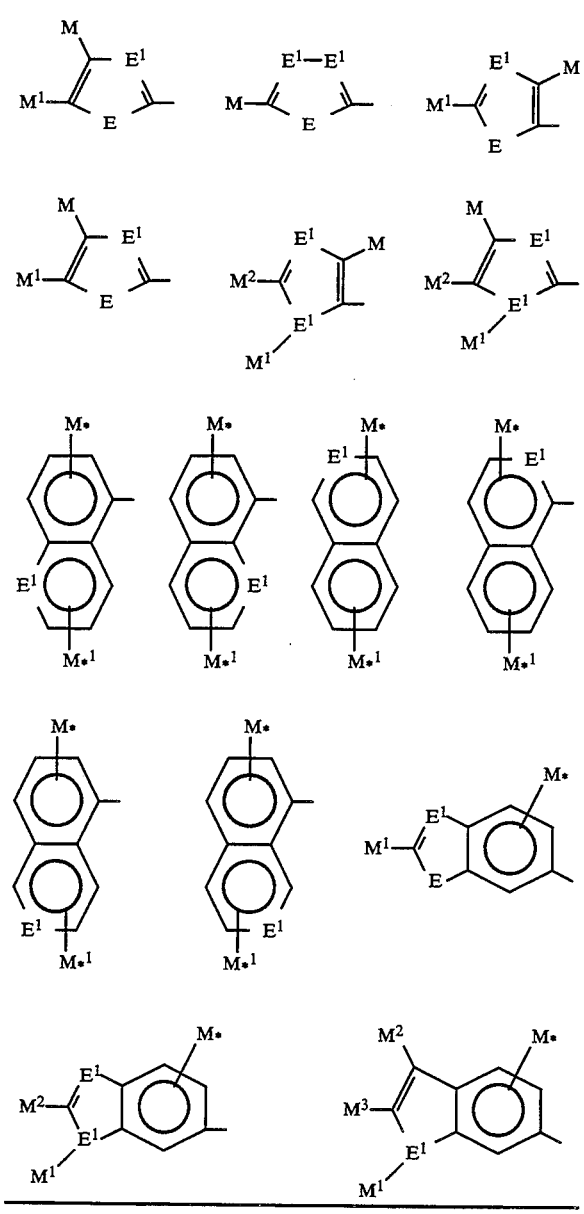
Each E = O, S, Se or Te. Each $E^1$ = N, P, As or Sb. Any of M, $M^1$ or $M^2$ is independently any one of J, L, $R^1$, $R^2$, G—$R^3$ or Q.
The subscript "*" signifies the number of available valences for the substituents.
TABLE 8
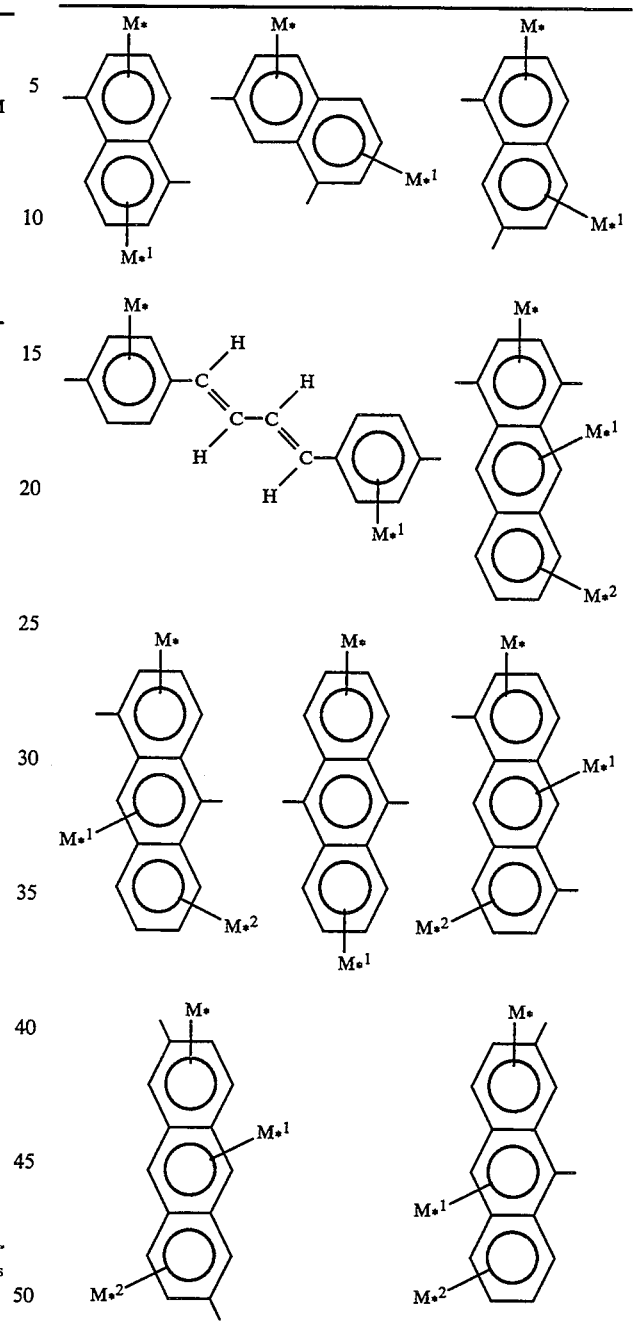
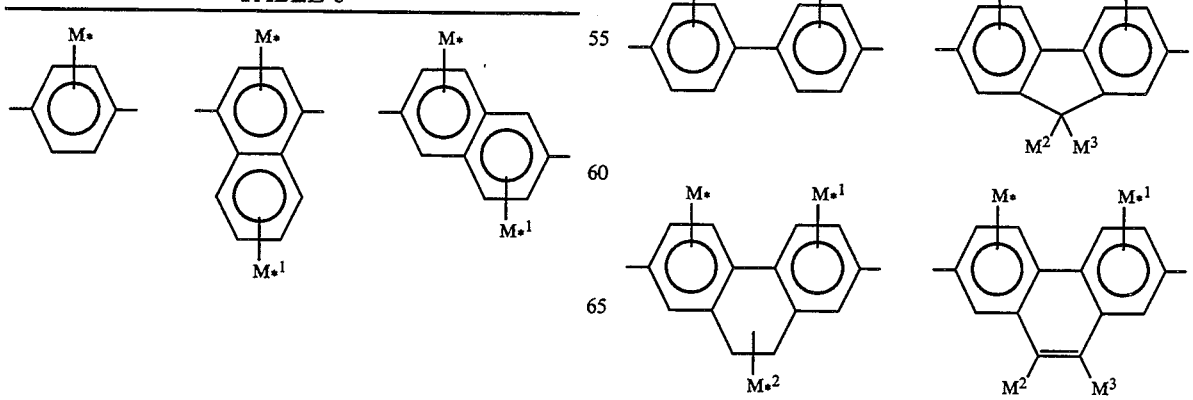

TABLE 8-continued

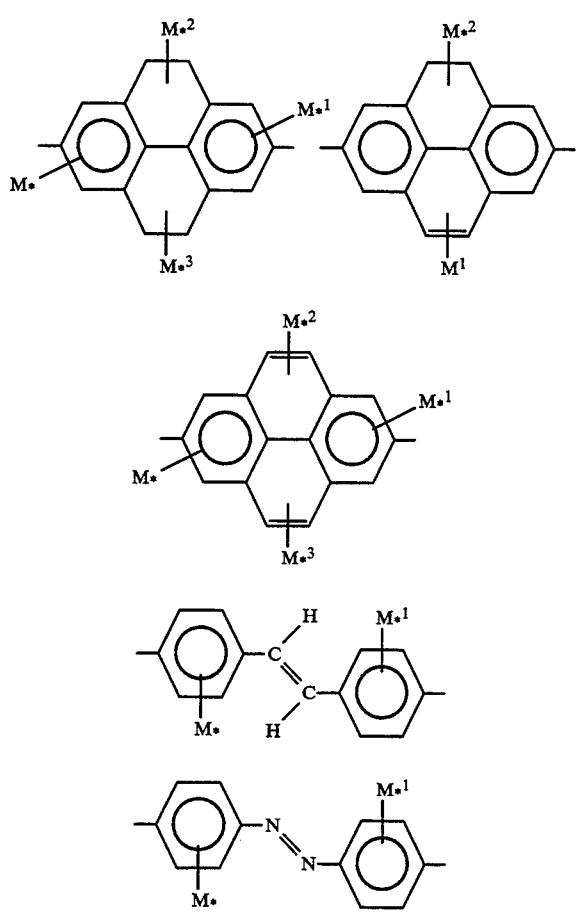

Any of M, M[1], M[2] or M[3] is independently any one of J, L, R[1], R[2], G—R[3] or Q. The subscript "*" signifies the number of available valences for the substituents.

TABLE 9

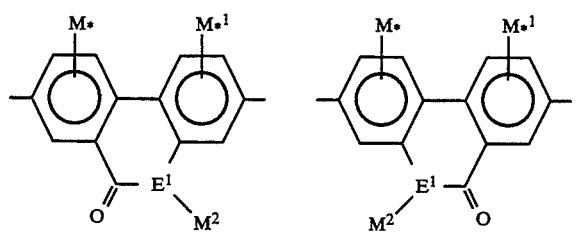

TABLE 9-continued

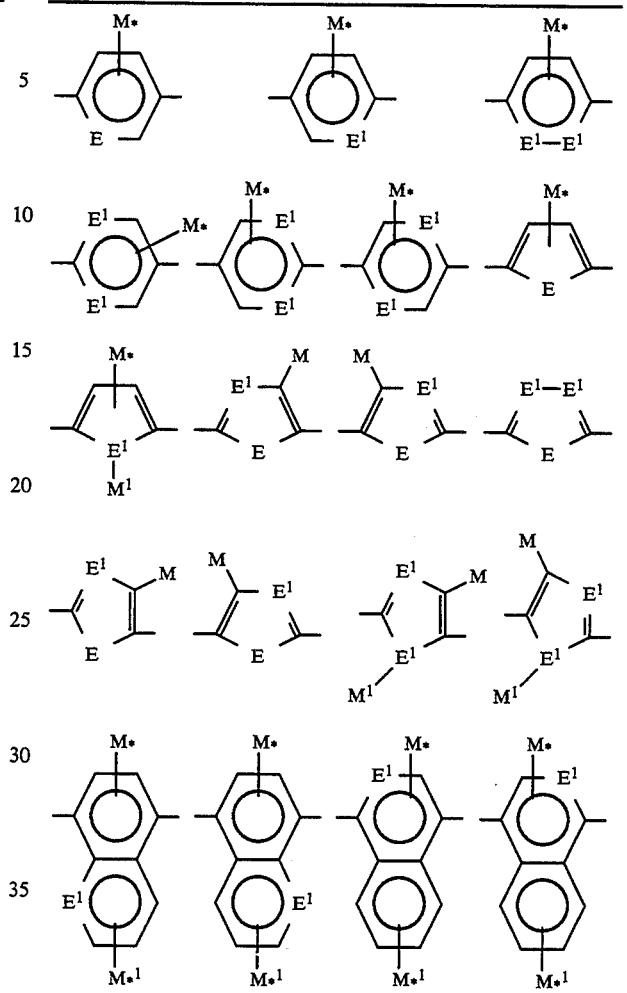

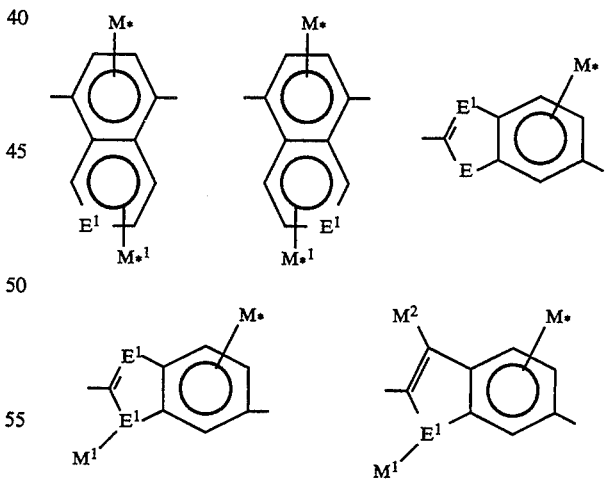

Each $E = O$, S, Se or Te. Each $E^1 = N$, P, As or Sb. Any of M, M[1], M[2] or M[3] is independently any one of J, L, R[1], R[2], G—R[3] or Q. The subscript "*" signifies the number of available valences for the substituents.

The present invention may be embodied in other specific forms without departing from the spirit or essential attributes thereof and, accordingly, reference should be made to the appended claims, rather than to the foregoing specification as indicating the scope of the invention.

I claim:

1. A process of making an aldehyde compound having a structure:

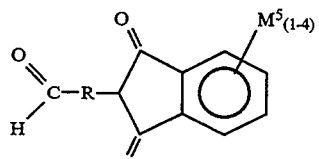

or

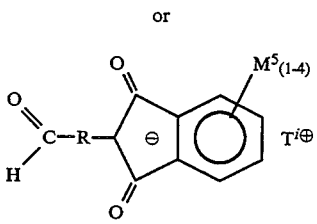

wherein R is a diradical comprising a substituted or unsubstituted aromatic carboxylic ring system of e members, where e is 6 to 20, or substituted or unsubstituted aromatic heterocyclic ring system of f members, where f is 4 to 20, wherein the substituents are zero to (e-2) or (f-2) same or different J, L, $R^1$, $R^2$, $G—R^3$ or Q substituents for the carbocyclic and heterocyclic ring systems, respectively;

G is a diradical comprising substituted or unsubstituted $—(—HC=CH—)_m—$, where m is an integer from 1 to 10, substituted or unsubstituted $—(CH_2—)_n—$, where n is an integer from 1 to 22, a substituted or unsubstituted aromatic ring system of 6 to 16 carbons or a substituted or unsubstituted aromatic heterocyclic ring system of g members, where g is 5 to 14, the members being carbon atoms and 1 to (g−1) heteroatoms, the heteroatom being one or more of N, P, As, Sb, O, S, Se or Te, the G substitutents being $J^1$ and $L^1$ with the proviso that the maximum number of G substituents is 6;

$G^1$ and $G^2$ each independently have the same definition as G;

J is an electron donating group $—(CH_2)_n—R^1$, $—S—R^1$, $—O—R^1$, $—N(R^1)(R^2)$, $—G—R^1$, $—(CH_2)_n—G—R^1$, $—S—G—R^1$, $—O—G—R^1$, $—N(G^1—R^1)(G^2—R^2)$;

$J^1$ is $—(CH_2)_n—R^1$, $—S—R^1$, $—O—R^1$ or $—N(R^1)(R^2)$;

$J^2$, $J^3$ and $J^4$ each independently have the same definition as J;

L is $—C\!\equiv\!N$, $—N\!=\!O$, $—NO_2$, $—C(=O)—J^2$,

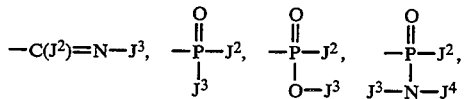

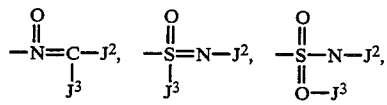

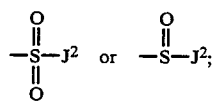

$L^1$ independently has the same definition as L;

$R^1$ and $R^2$ are independently H, F, Cl, Br, I, Q, alkyl of 1 to 22 carbons, cycloalkyl of 3 to 22 carbons, a substituted or unsubstituted aromatic ring system of 6 to 16 carbons or a substituted or unsubstituted aromatic heterocyclic ring system of h members in the ring system, where h is 5 to 14, the members being carbon atoms and 1 to (h−1) heteroatoms, the heteroatom being one or more of N, P, As, Sb, O, S, Se or Te, the $R^1$ or $R^2$ substituents being $J^1$ or $L^1$ with the proviso that the maximum number of $R^1$ or $R^2$ substituents is 6;

$R^3$ is H, F, Cl, Br, I, Q, alkyl of 1 to 22 carbons or cycloalkyl of 3 to 22 carbons;

Q is a polymerizable group, the polymerizable group being alpha,beta-unsaturated carbonyl of 4 to 26 carbons, vinyl ether of 3 to 25 carbons, carboxylic acid of 2 to 23 carbons, ester of 3 to 45 carbons, alcohol of 1 to 22 carbons, alkyl amine of 1 to 44 carbons, 1-substituted or 1,1-substituted alkylene of 2 to 44 carbons, or a polymerizable group of 1 to 44 carbons containing a nucleophilically replaceable group of zero to 22 carbons, the nucleophilically replaceable group being F, Cl, Br, I, an alkyl halide or an $—O—L$ group, the Q substituents being J, L, $R^1$, $R^2$, $G—R^3$, any $M^5$ independently is any of J, L, $R^1$, $R^2$, $G—R^3$ or Q;

$T^{i\oplus}$ is a stable metallic or nonmetallic cation; and i is an integer of 1 to 4;

the process comprising (a) reacting a first starting material having a structure

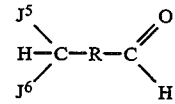

where $J^5$ and $J^6$ are independently $—S—R^1$, $—OR^1$, or $—N(R^1)(R^2)$, with a substituted or unsubstituted phthalide having a structure

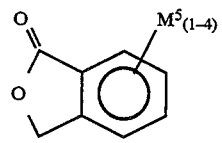

in the presence of a strong base and an organic solvent for the reactants and base;

(b) heating the reaction mixture of step (a) at a sufficient temperature and for a sufficient time to obtain an intermediate reaction product;

(c) heating the intermediate reaction product of step (b) in the presence of a mineral acid at a sufficient temperature and for a sufficient time to obtain the aldehyde compound; and (d) isolating the aldehyde compound.

2. The process of claim 1 wherein, where R is a substituted or unsubstituted diradical comprising an aromatic carbocyclic ring system, the aromatic carbocyclic ring system is any $R^8$ diradical as follows, where any of M, $M^1$, $M^2$ or $M^3$ is independently any one of J, L, $R^1$, $R^2$, $G—R^3$ or Q, and the subscript "*" signifies the number of available valences for the substituents:

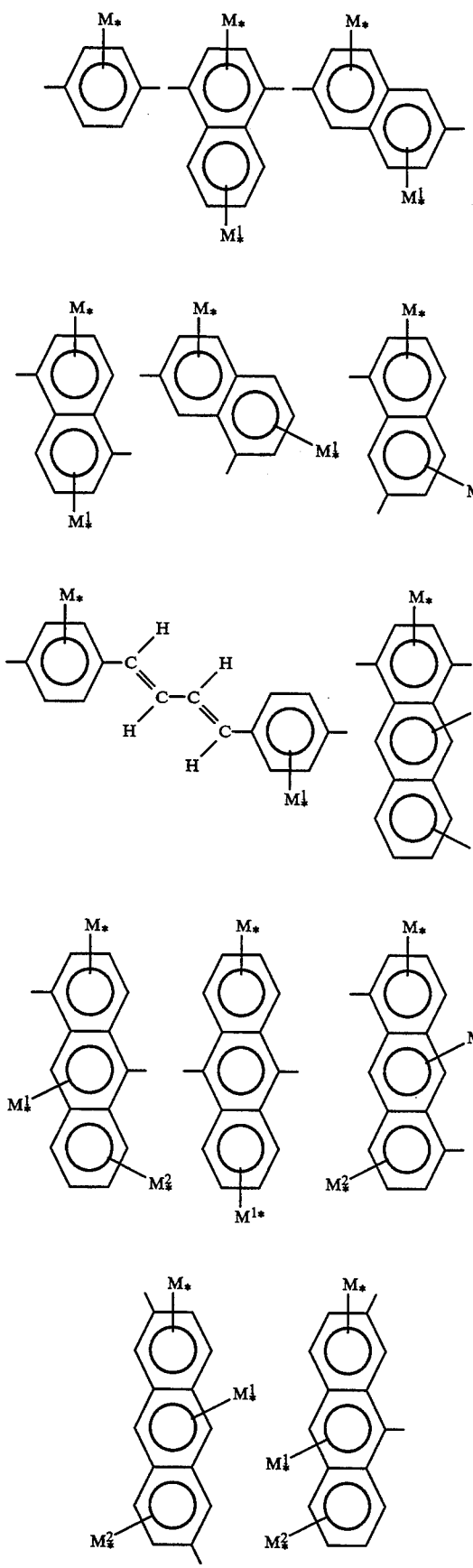
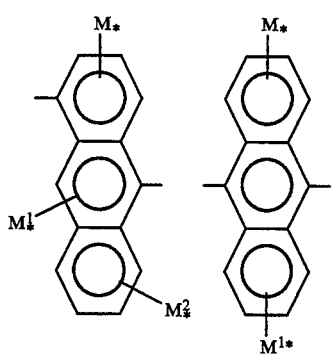
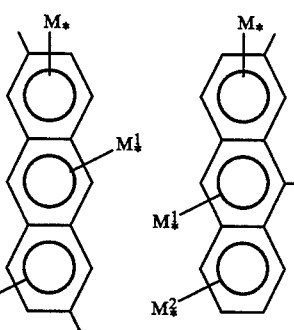
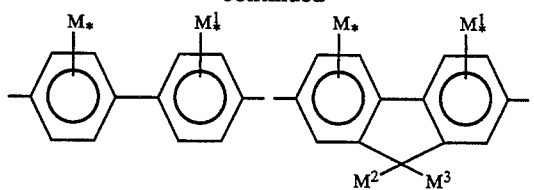
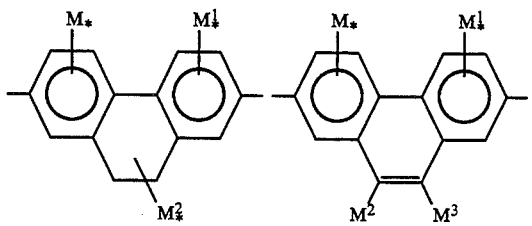
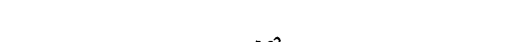
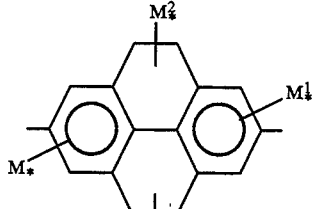
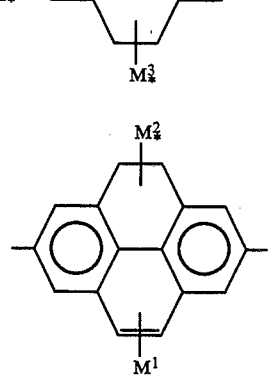
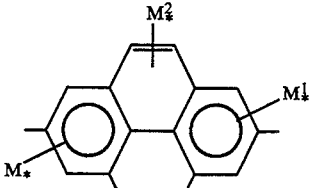
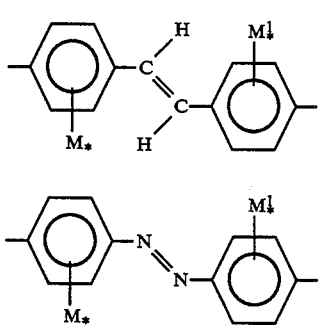
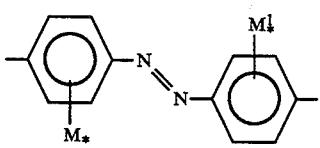
and when R is a substituted or unsubstituted aromatic heterocyclic ring system, the heterocyclic ring system is any diradical $R^9$ as follows, where any $E^1$ is N, P or As, any E is O, S, Se or Te, any of M, $M^1$ or $M^2$ is independently any one of J, L, $R^1$, $R^2$, G—$R^3$ or Q, and the subscript "*" signifies the number of available valences for the substituents:

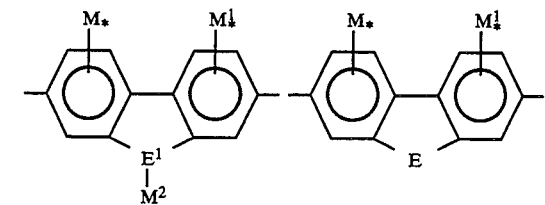
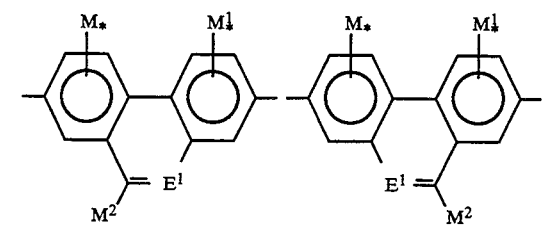
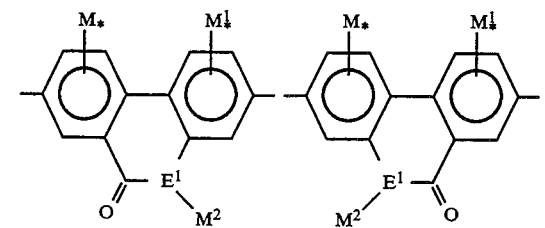
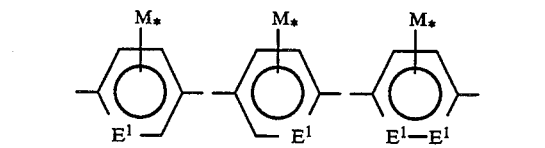
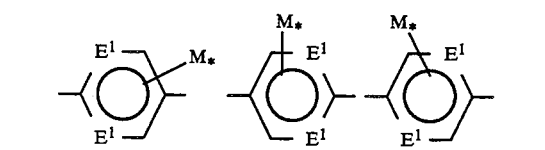
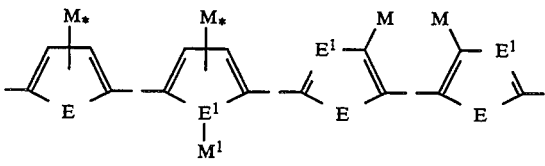
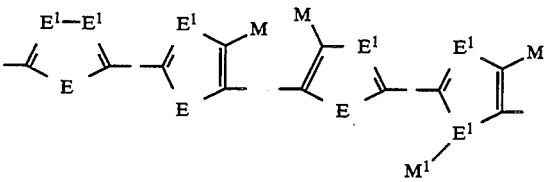

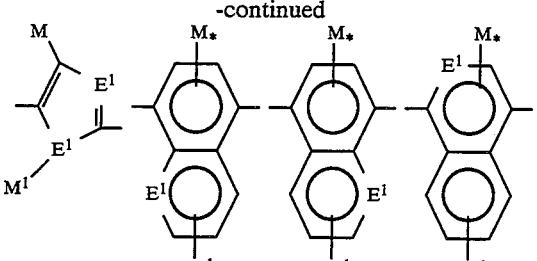
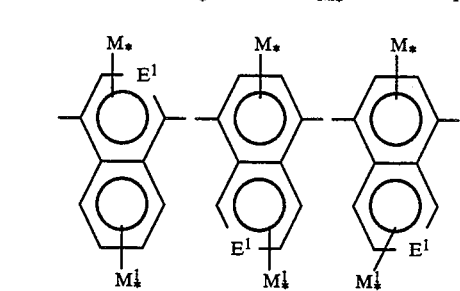
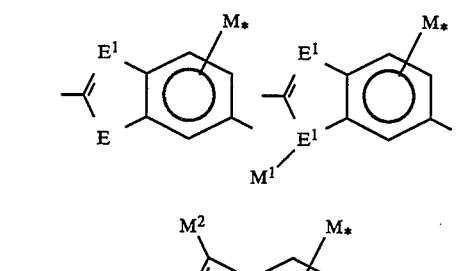
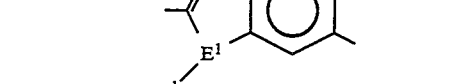
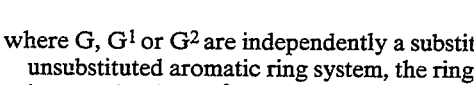
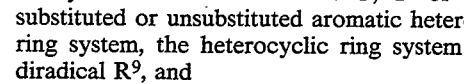
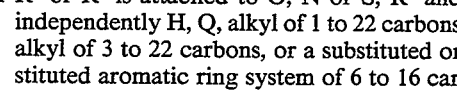

where G, $G^1$ or $G^2$ are independently a substituted or unsubstituted aromatic ring system, the ring system is any diradical $R^8$ and where G, $G^1$ or $G^2$ is a substituted or unsubstituted aromatic heterocyclic ring system, the heterocyclic ring system is any diradical $R^9$, and if $R^1$ or $R^2$ is attached to O, N or S, $R^1$ and $R^2$ are independently H, Q, alkyl of 1 to 22 carbons, cycloalkyl of 3 to 22 carbons, or a substituted or unsubstituted aromatic ring system of 6 to 16 carbons or a substituted or unsubstituted aromatic heterocyclic ring system of h members in the ring system, where h is 5 to 14, the members being carbon atoms and 1 to (h-1) heteroatoams, the heteroatom being one or more of N, P, As, Sb, O, S, Se or Te, the $R^1$ or $R^2$ substituents being $J^1$ or $L^1$ with the proviso that the maximum number of $R^1$ or $R^2$ substituents is 6.

3. The process of claim 2, wherein in any $R^9$ diradical, any $E^1$ is N and any E is O or S.

4. The process of claim 1, wherein the mineral acid of step (c) is in a solution of an organic acid.

5. The process of claim 2, wherein the mineral acid of step (c) is in a solution of an organic acid.

6. The process of claim 3, wherein the mineral acid of step (c) is in a solution of an organic acid.

* * * * *